(12) United States Patent
Matulic-Adamic et al.

(10) Patent No.: US 8,461,313 B2
(45) Date of Patent: Jun. 11, 2013

(54) CONJUGATES AND COMPOSITIONS FOR CELLULAR DELIVERY

(75) Inventors: Jasenka Matulic-Adamic, Ann Arbor, MI (US); Leonid Beigelman, San Mateo, CA (US)

(73) Assignee: Sirna Therapeutics, Inc., San Francisco, CA (US)

( * ) Notice: Subject to any disclaimer, the term of this patent is extended or adjusted under 35 U.S.C. 154(b) by 0 days.

(21) Appl. No.: 13/456,430

(22) Filed: Apr. 26, 2012

(65) Prior Publication Data

US 2012/0202983 A1  Aug. 9, 2012

Related U.S. Application Data

(60) Continuation of application No. 12/871,750, filed on Aug. 30, 2010, now Pat. No. 8,188,247, which is a continuation of application No. 11/166,717, filed on Jun. 24, 2005, now Pat. No. 7,858,625, which is a division of application No. 10/151,116, filed on May 17, 2002, now Pat. No. 7,109,165.

(60) Provisional application No. 60/362,016, filed on Mar. 6, 2002, provisional application No. 60/292,217, filed on May 18, 2001.

(51) Int. Cl.
*C07H 19/00* (2006.01)
*C07H 21/00* (2006.01)

(52) U.S. Cl.
USPC ........................................................ 536/22.1

(58) Field of Classification Search
None
See application file for complete search history.

(56) References Cited

U.S. PATENT DOCUMENTS

| 6,022,962 | A  | * | 2/2000 | Chowrira et al. | 536/24.5 |
| 6,335,434 | B1 | * | 1/2002 | Guzaev et al. | 536/23.1 |
| 6,749,863 | B1 | * | 6/2004 | Chang et al. | 424/450 |
| 7,109,165 | B2 | * | 9/2006 | Matulic-Adamic et al. | 424/94.1 |
| 7,858,625 | B2 | * | 12/2010 | Matulic-Adamic et al. | 514/243 |
| 8,188,247 | B2 | * | 5/2012 | Beigelman et al. | 536/23.2 |

* cited by examiner

*Primary Examiner* — Marcela M Cordero Garcia
(74) *Attorney, Agent, or Firm* — Yong Zhao; David A. Muthard

(57) ABSTRACT

This invention features conjugates, compositions, methods of synthesis, and applications thereof, including folate derived conjugates of nucleosides, nucleotides, non-nucleosides, and nucleic acids including enzymatic nucleic acids and antisense nucleic acid molecules.

11 Claims, 12 Drawing Sheets

*Figure 3: Stabilized Zinzyme Ribozyme Motif*

Figure 4: DNAzyme Motif

Figure 5: Synthesis of Folate Linked phosphoramidite

Figure 6: Fludarabine-Folate conjugates

Figure 7: Solid Phase Post-synthetic conjugation of pteroic acid

Figure 8: Chemo-enzymatic synthesis of pteroic acid synthon

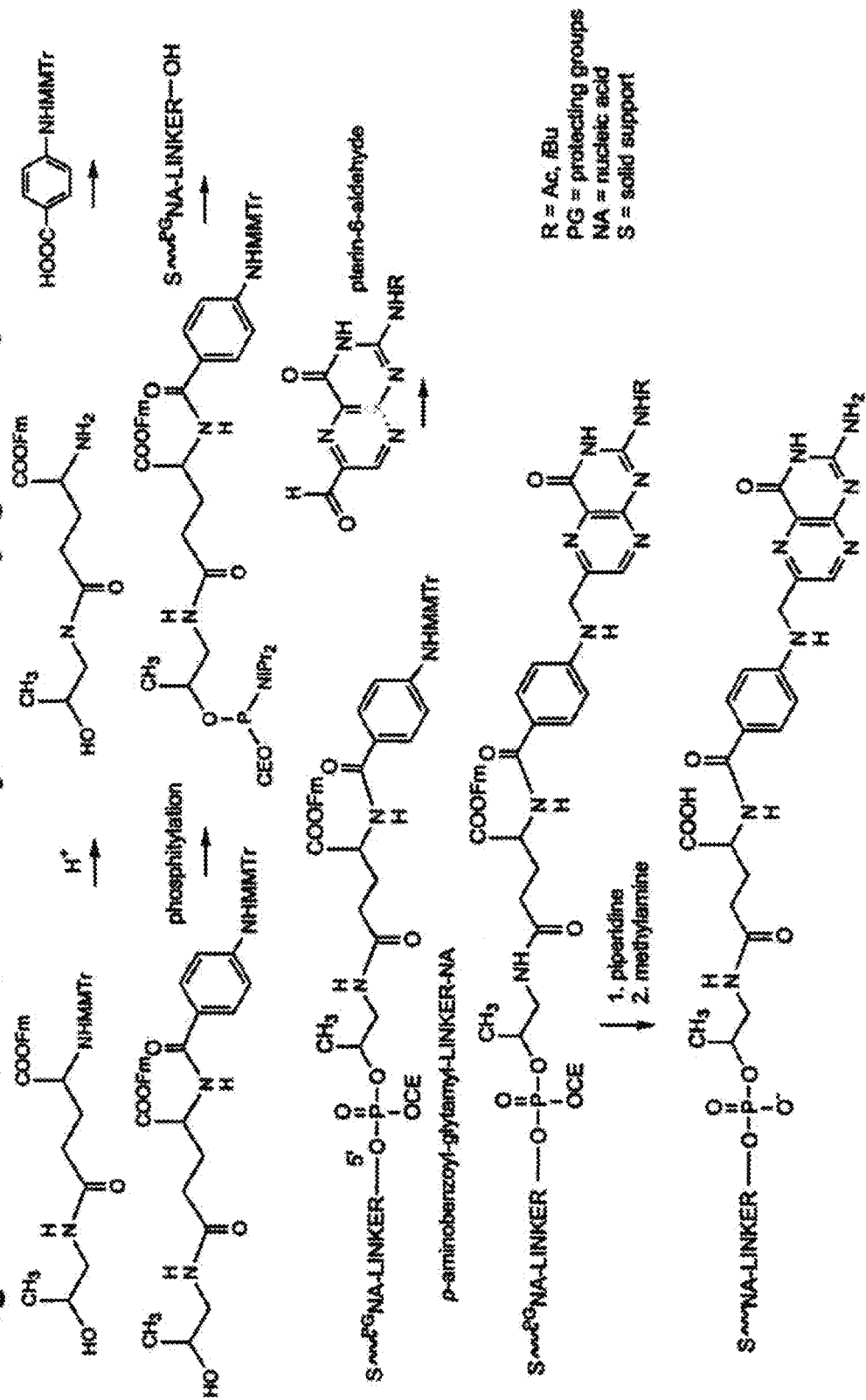
Figure 12: Solid Phase Post-synthetic conjugation of pteroic acid

SEQUENCE LISTING

<160> NUMBER OF SEQ ID NOS: 12

<210> SEQ ID NO 1
<211> LENGTH: 10
<212> TYPE: RNA
<213> ORGANISM: Artificial Sequence
<220> FEATURE:
<223> OTHER INFORMATION: Synthetic

<400> SEQUENCE: 1
gccguuaggc                                                                                    10

<210> SEQ ID NO 2
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(6)
<223> OTHER INFORMATION: n can be any nucleotide
<220> FEATURE:
<221> NAME/KEY: misc_feature
<222> LOCATION: (9)..(15)
<223> OTHER INFORMATION: n can be any nucleotide

<400> SEQUENCE: 2
nnnnnnuhnn nnnnn                                                                              15

<210> SEQ ID NO 3
<211> LENGTH: 36
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(7)
<223> OTHER INFORMATION: n can be any nucleotide
<220> FEATURE:
<221> NAME/KEY: misc_feature
<222> LOCATION: (1)..(8)
<223> OTHER INFORMATION: 2'-O'methyl
<220> FEATURE:
<221> NAME/KEY: misc_feature
<222> LOCATION: (9)..(9)
<223> OTHER INFORMATION: 2'-deoxy-2'-C-Allyl
<220> FEATURE:
<221> NAME/KEY: misc_feature
<222> LOCATION: (12)..(12)
<223> OTHER INFORMATION: 2'-O'methyl
<220> FEATURE:
<221> NAME/KEY: misc_feature
<222> LOCATION: (14)..(26)
<223> OTHER INFORMATION: 2'-O'methyl
<220> FEATURE:
<221> NAME/KEY: misc_feature
<222> LOCATION: (16)..(18)
<223> OTHER INFORMATION: n can be any nucleotide
<220> FEATURE:
<221> NAME/KEY: misc_feature
<222> LOCATION: (23)..(25)
<223> OTHER INFORMATION: n can be any nucleotide
<220> FEATURE:
<221> NAME/KEY: misc_feature
<222> LOCATION: (28)..(29)
<223> OTHER INFORMATION: 2'-O'methyl
<220> FEATURE:
<221> NAME/KEY: misc_feature
<222> LOCATION: (31)..(36)
<223> OTHER INFORMATION: n can be any nucleotide
<220> FEATURE:
<221> NAME/KEY: misc_feature
<222> LOCATION: (31)..(36)
<223> OTHER INFORMATION: 2'-O'methyl

<400> SEQUENCE: 3
nnnnnnncug augagnnnga aannncgaaa nnnnnn                                                       36

<210> SEQ ID NO 4
<211> LENGTH: 14
<212> TYPE: RNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (1)..(5)
<223> OTHER INFORMATION: n stands for any nucleotide
<220> FEATURE:
<221> NAME/KEY: misc_feature
<222> LOCATION: (8)..(14)
<223> OTHER INFORMATION: n stands for any nucleotide

<400> SEQUENCE: 4
nnnnnchnnn nnnn                                                              14

<210> SEQ ID NO 5
<211> LENGTH: 35
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(7)
<223> OTHER INFORMATION: n can be any nucleotide
<220> FEATURE:
<221> NAME/KEY: misc_feature
<222> LOCATION: (1)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-C-Allyl
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(26)
<223> OTHER INFORMATION: 2'-O-methyl
<220> FEATURE:
<221> NAME/KEY: misc_feature
<222> LOCATION: (16)..(18)
<223> OTHER INFORMATION: n can be any nucleotide
<220> FEATURE:
<221> NAME/KEY: misc_feature
<222> LOCATION: (23)..(25)
<223> OTHER INFORMATION: n can be any nucleotide
<220> FEATURE:
<221> NAME/KEY: misc_feature
<222> LOCATION: (28)..(29)
<223> OTHER INFORMATION: 2'-O-methyl
<220> FEATURE:
<221> NAME/KEY: misc_feature
<222> LOCATION: (30)..(30)
<223> OTHER INFORMATION: inosine
<220> FEATURE:
<221> NAME/KEY: misc_feature
<222> LOCATION: (31)..(35)
<223> OTHER INFORMATION: n can be any nucleotide
<220> FEATURE:
<221> NAME/KEY: misc_feature
<222> LOCATION: (31)..(35)
<223> OTHER INFORMATION: 2'-O-methyl

<400> SEQUENCE: 5
nnnnnnncug augagnnnga aannncgaan nnnnn                                       35

<210> SEQ ID NO 6
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(6)
```

```
<223> OTHER INFORMATION: n can be any nucleotide
<220> FEATURE:
<221> NAME/KEY: misc_feature
<222> LOCATION: (9)..(15)
<223> OTHER INFORMATION: n can be any nucleotide

<400> SEQUENCE: 6
nnnnnnygnn nnnnn                                                           15

<210> SEQ ID NO 7
<211> LENGTH: 35
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(7)
<223> OTHER INFORMATION: n can be any nucleotide
<220> FEATURE:
<221> NAME/KEY: misc_feature
<222> LOCATION: (1)..(8)
<223> OTHER INFORMATION: 2'-O-methyl
<220> FEATURE:
<221> NAME/KEY: misc_feature
<222> LOCATION: (11)..(11)
<223> OTHER INFORMATION: phosphorothioate 3'-internucleotide linkage
<220> FEATURE:
<221> NAME/KEY: misc_feature
<222> LOCATION: (13)..(16)
<223> OTHER INFORMATION: 2'-O-methyl
<220> FEATURE:
<221> NAME/KEY: misc_feature
<222> LOCATION: (18)..(35)
<223> OTHER INFORMATION: 2'-O-methyl
<220> FEATURE:
<221> NAME/KEY: misc_feature
<222> LOCATION: (29)..(35)
<223> OTHER INFORMATION: n can be any nucleotide

<400> SEQUENCE: 7
nnnnnnnuga uggcaugcac uaugcgcgnn nnnnn                                      35

<210> SEQ ID NO 8
<211> LENGTH: 48
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: 2'-O-methyl
<220> FEATURE:
<221> NAME/KEY: misc_feature
<222> LOCATION: (9)..(10)
<223> OTHER INFORMATION: 2'-deoxy-2'-amino
<220> FEATURE:
<221> NAME/KEY: misc_feature
<222> LOCATION: (12)..(21)
<223> OTHER INFORMATION: 2'-O-methyl
<220> FEATURE:
<221> NAME/KEY: misc_feature
<222> LOCATION: (22)..(26)
<223> OTHER INFORMATION: 2'-deoxy-2'-amino
<220> FEATURE:
<221> NAME/KEY: misc_feature
<222> LOCATION: (32)..(37)
<223> OTHER INFORMATION: 2'-O-methyl
<220> FEATURE:
<221> NAME/KEY: misc_feature
<222> LOCATION: (38)..(40)
<223> OTHER INFORMATION: 2'-deoxy-2'-amino
<220> FEATURE:
<221> NAME/KEY: misc_feature
<222> LOCATION: (44)..(48)
```

<223> OTHER INFORMATION: 2'-O-methyl

<400> SEQUENCE: 8
gugugcaacc ggaggaaacu cccuucaagg acgaaagucc gggacggg         48

<210> SEQ ID NO 9
<211> LENGTH: 16
<212> TYPE: RNA
<213> ORGANISM: Artificial Sequence
<220> FEATURE:
<223> OTHER INFORMATION: Synthetic

<400> SEQUENCE: 9
gccguggguu gcacac         16

<210> SEQ ID NO 10
<211> LENGTH: 35
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(7)
<223> OTHER INFORMATION: 2'-O-methyl
<220> FEATURE:
<221> NAME/KEY: misc_feature
<222> LOCATION: (1)..(4)
<223> OTHER INFORMATION: phosphorothioate 3'-internucleotide linkage
<220> FEATURE:
<221> NAME/KEY: misc_feature
<222> LOCATION: (9)..(15)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-amino
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (21)..(21)
<223> OTHER INFORMATION: 2'-O-methyl
<220> FEATURE:
<221> NAME/KEY: misc_feature
<222> LOCATION: (23)..(23)
<223> OTHER INFORMATION: 2'-O-methyl
<220> FEATURE:
<221> NAME/KEY: misc_feature
<222> LOCATION: (26)..(26)
<223> OTHER INFORMATION: 2'-O-methyl
<220> FEATURE:
<221> NAME/KEY: misc_feature
<222> LOCATION: (27)..(27)
<223> OTHER INFORMATION: 2'-deoxy-2'-amino
<220> FEATURE:
<221> NAME/KEY: misc_feature
<222> LOCATION: (28)..(35)
<223> OTHER INFORMATION: 2'-O-methyl
<220> FEATURE:
<221> NAME/KEY: misc_feature
<222> LOCATION: (35)..(35)
<223> OTHER INFORMATION: deoxyabasic moiety

<400> SEQUENCE: 10
gugccuggcc gaaaggcgag ugaggucugc cgcgc         35

<210> SEQ ID NO 11
<211> LENGTH: 15
<212> TYPE: RNA
<213> ORGANISM: Artificial Sequence
<220> FEATURE:

```
<223> OTHER INFORMATION: Synthetic

<400> SEQUENCE: 11
gcgcggcgca ggcac                                                     15

<210> SEQ ID NO 12
<211> LENGTH: 16
<212> TYPE: DNA
<213> ORGANISM: Artificial Sequence
<220> FEATURE:
<223> OTHER INFORMATION: Synthetic

<400> SEQUENCE: 12
rggctagcta caacga                                                    16
```

CONJUGATES AND COMPOSITIONS FOR CELLULAR DELIVERY

This patent application is a divisional of U.S. Ser. No. 10/151,116, filed May 17, 2002 which claims priority from U.S. Ser. No. 60/362,016, filed Mar. 6, 2002 and from U.S. Ser. No. 60/292,217, filed May 18, 2001, both entitled 'CONJUGATES AND COMPOSITIONS FOR CELLULAR DELIVERY'. These applications are hereby incorporated by reference herein in their entirety including the drawings.

REFERENCE TO SEQUENCE LISTING SUBMITTED ELECTRONICALLY

The sequence listing of the present application is being submitted electronically via EFS-Web as an ASCII formatted sequence listing with a file name "SIRMIS00003USCNT5-SEQTXT.txt", creation date of Apr. 25, 2012 and a size of 6,429 bytes. This sequence listing submitted via EFS-Web is part of the specification and is herein incorporated by reference in its entirety.

BACKGROUND OF THE INVENTION

The present invention relates to conjugates, compositions, methods of synthesis, and applications thereof. The discussion is provided only for understanding of the invention that follows. This summary is not an admission that any of the work described below is prior art to the claimed invention.

The cellular delivery of various therapeutic compounds, such as antiviral and chemotherapeutic agents, is usually compromised by two limitations. First the selectivity of chemotherapeutic agents is often low, resulting in high toxicity to normal tissues. Secondly, the trafficking of many compounds into living cells is highly restricted by the complex membrane systems of the cell. Specific transporters allow the selective entry of nutrients or regulatory molecules, while excluding most exogenous molecules such as nucleic acids and proteins. Various strategies can be used to improve transport of compounds into cells, including the use of lipid carriers and various conjugate systems. Conjugates are often selected based on the ability of certain molecules to be selectively transported into specific cells, for example via receptor mediated endocytosis. By attaching a compound of interest to molecules that are actively transported across the cellular membranes, the effective transfer of that compound into cells or specific cellular organelles can be realized. Alternately, molecules that are able to penetrate cellular membranes without active transport mechanisms, for example, various lipophilic molecules, can be used to deliver compounds of interest. Examples of molecules that can be utilized as conjugates include but are not limited to peptides, hormones, fatty acids, vitamins, flavonoids, sugars, reporter molecules, reporter enzymes, chelators, porphyrins, intercalcators, and other molecules that are capable of penetrating cellular membranes, either by active transport or passive transport.

The delivery of compounds to specific cell types, for example, cancer cells, can be accomplished by utilizing receptors associated with specific cell types. Particular receptors are overexpressed in certain cancerous cells, including the high affinity folic acid receptor. For example, the high affinity folate receptor is a tumor marker that is overexpressed in a variety of neoplastic tissues, including breast, ovarian, cervical, colorectal, renal, and nasoparyngeal tumors, but is expressed to a very limited extent in normal tissues. The use of folic acid based conjugates to transport exogenous compounds across cell membranes can provide a targeted delivery approach to the treatment and diagnosis of disease and can provide a reduction in the required dose of therapeutic compounds. Furthermore, therapeutic bioavialability, pharmacodynamics, and pharmacokinetic parameters can be modulated through the use of bioconjugates, including folate bioconjugates. Godwin et al., 1972, *J. Biol. Chem.*, 247, 2266-2271, report the synthesis of biologically active pteroyloligo-L-glutamates. Habus et al., 1998, *Bioconjugate Chem.*, 9, 283-291, describe a method for the solid phase synthesis of certain oligonucleotide-folate conjugates. Cook, U.S. Pat. No. 6,721,208, describes certain oligonucleotides modified with specific conjugate groups. The use of biotin and folate conjugates to enhance transmembrane transport of exogenous molecules, including specific oligonucleotides has been reported by Low et al., U.S. Pat. Nos. 5,416,016, 5,108,921, and International PCT publication No. WO 90/12096. Manoharan et al., International PCT publication No. WO 99/66063 describe certain folate conjugates, including specific nucleic acid folate conjugates with a phosphoramidite moiety attached to the nucleic acid component of the conjugate, and methods for the synthesis of these folate conjugates. Nomura et al., 2000, *J. Org. Chem.*, 65, 5016-5021, describe the synthesis of an intermediate, alpha-[2-(trimethylsilyl) ethoxycarbonl]folic acid, useful in the synthesis of certain types of folate-nucleoside conjugates. Guzaev et al., U.S. Pat. No. 6,335,434, describes the synthesis of certain folate oligonucleotide conjugates.

SUMMARY OF THE INVENTION

The present invention features a compound having the formula I:

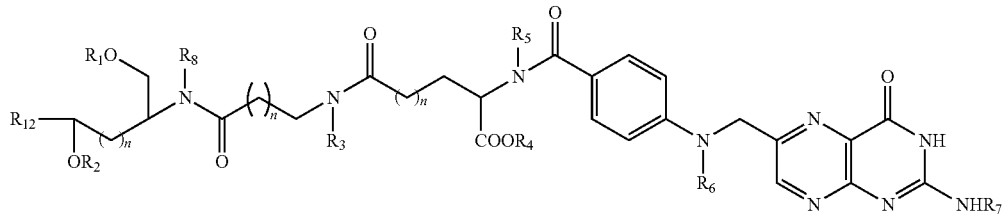

wherein each $R_1$, $R_3$, $R_4$, $R_5$, $R_6$, $R_7$ and $R_8$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a phosphorus containing group, nucleoside, nucleotide, small molecule, nucleic acid, or a solid support comprising a linker.

The present invention features a compound having the formula II:

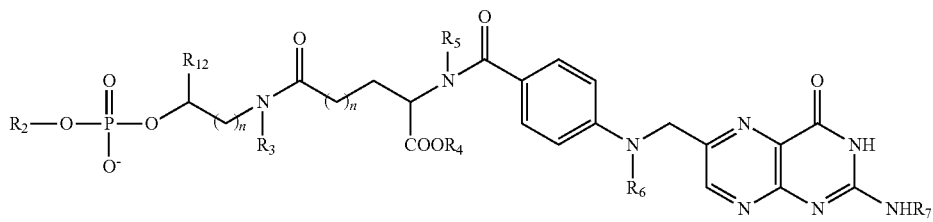

wherein each $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a phosphorus containing group, nucleoside, nucleotide, small molecule, nucleic acid, or a solid support comprising a linker.

The present invention features a compound having the formula III:

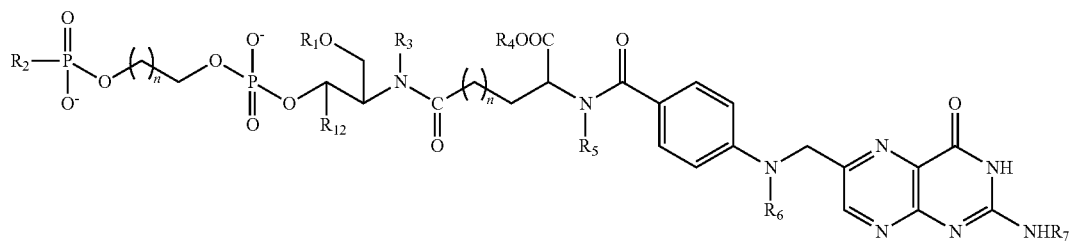

wherein each $R_1$, $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a phosphorus containing group, nucleoside, nucleotide, small molecule, or nucleic acid.

The present invention features a compound having the formula IV:

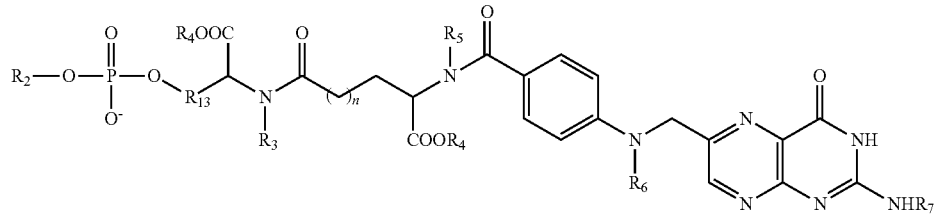

wherein each $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_2$ is a phosphorus containing group, nucleoside, nucleotide, small molecule, nucleic acid, or a solid support comprising a linker, and $R_{13}$ is an amino acid side chain.

The present invention features a compound having the formula V:

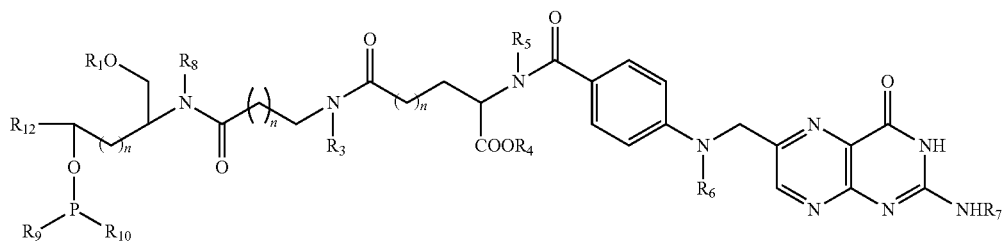

wherein each $R_1$ and $R_4$ is independently a protecting group or hydrogen, each $R_3$, $R_5$, $R_6$, $R_7$ and $R_8$ is independently hydrogen, alkyl or nitrogen protecting group, each "n" is independently an integer from 0 to about 200, $R_{12}$ is a straight or branched chain alkyl, substituted alkyl, aryl, or substituted aryl, and each $R_9$ and $R_{10}$ is independently a nitrogen containing group, cyanoalkoxy, alkoxy, aryloxy, or alkyl group.

The present invention features a compound having the formula VI:

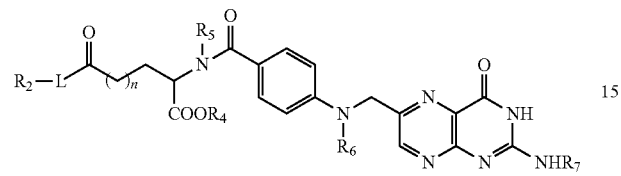

wherein each $R_4$, $R_5$, $R_6$ and $R_7$ is independently hydrogen, alkyl, substituted alkyl, aryl, substituted aryl, or a protecting group, $R_2$ is a phosphorus containing group, nucleoside, nucleotide, small molecule, nucleic acid, or a solid support comprising a linker, each "n" is independently an integer from 0 to about 200, and L is a degradable linker.

The present invention features a compound having the formula VII:

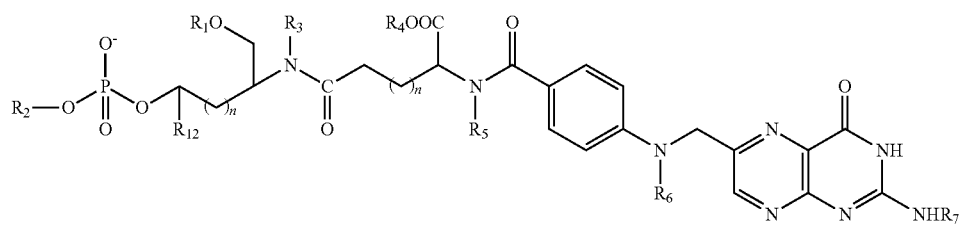

wherein each $R_1$, $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a phosphorus containing group, nucleoside, nucleotide, small molecule, nucleic acid, or a solid support comprising a linker.

The present invention features a compound having the formula VIII:

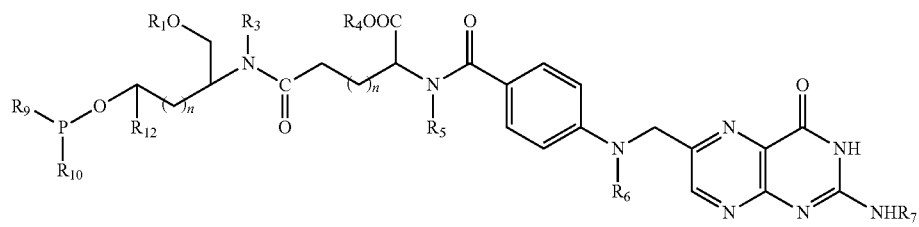

wherein each $R_1$ and $R_4$ is independently a protecting group or hydrogen, each $R_3$, $R_5$, $R_6$ and $R_7$ is independently hydrogen, alkyl or nitrogen protecting group, each "n" is independently an integer from 0 to about 200, $R_{12}$ is a straight or branched chain alkyl, substituted alkyl, aryl, or substituted aryl, and each $R_9$ and $R_{10}$ is independently a nitrogen containing group, cyanoalkoxy, alkoxy, aryloxy, or alkyl group.

The present invention features a method for synthesizing a compound having Formula V:

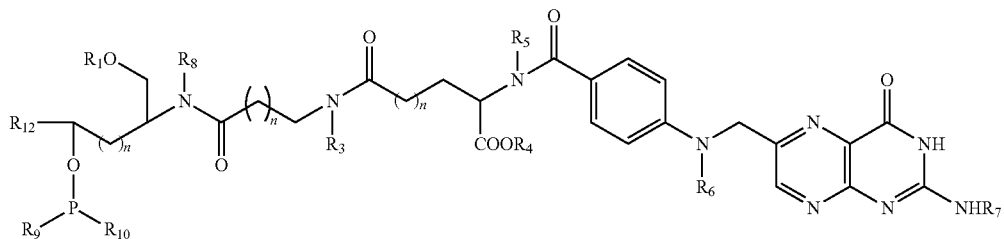

wherein each $R_1$ and $R_4$ is independently a protecting group or hydrogen, each $R_3$, $R_5$, $R_6$ and $R_7$ is independently hydrogen, alkyl or nitrogen protecting group, each "n" is independently an integer from 0 to about 200, $R_{12}$ is a straight or branched chain alkyl, substituted alkyl, aryl, or substituted aryl, and each $R_9$ and $R_{10}$ is independently a nitrogen containing group, cyanoalkoxy, alkoxy, aryloxy, or alkyl group, comprising: coupling a bis-hydroxy aminoalkyl derivative, for example D-threoninol, with a N-protected aminoalkanoic acid to yield a compound of Formula IX;

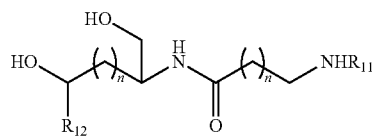

wherein $R_{11}$ is an amino protecting group, $R_{12}$ is a straight or branched chain alkyl, substituted alkyl, aryl, or substituted aryl, and each "n" is independently an integer from 0 to about 200; introducing primary hydroxy protection $R_1$ followed by amino deprotection of $R_{11}$ to yield a compound of Formula X;

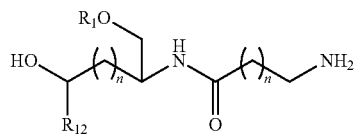

wherein $R_1$ is a protecting group, $R_{12}$ is a straight or branched chain alkyl, substituted alkyl, aryl, or substituted aryl, and each "n" is independently an integer from 0 to about 200; coupling the deprotected amine of Formula X with a protected amino acid, for example glutamic acid, to yield a compound of Formula XI;

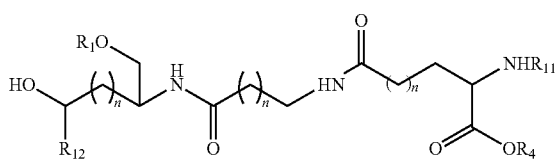

wherein each $R_1$ and $R_4$ is independently a protecting group or hydrogen, each "n" is independently an integer from 0 to about 200, $R_{11}$ is an amino protecting group, and $R_{12}$ is a straight or branched chain alkyl, substituted alkyl, aryl, or substituted aryl; deprotecting the amine $R_{11}$ of the conjugated glutamic acid of Formula XI to yield a compound of Formula XII;

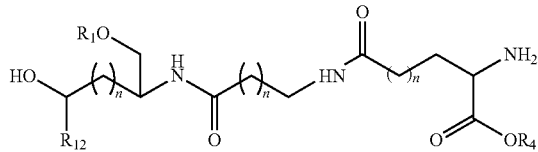

wherein each $R_1$ and $R_4$ is independently a protecting group or hydrogen, each "n" is independently an integer from 0 to about 200, $R_{11}$ is an amino protecting group, and $R_{12}$ is a straight or branched chain alkyl, substituted alkyl, aryl, or substituted aryl; coupling the deprotected amine of Formula XII with an amino protected pteroic acid to yield a compound of Formula XIII;

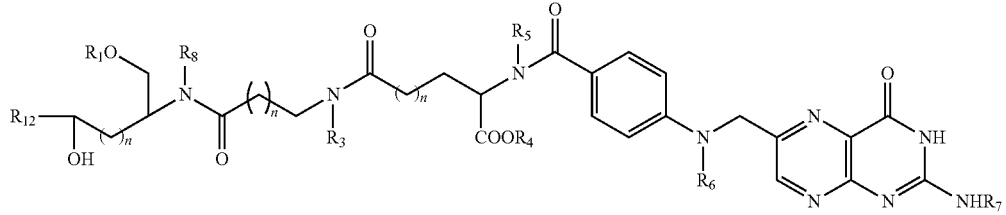

wherein each $R_1$ and $R_4$ is independently a protecting group or hydrogen, each $R_3$, $R_5$, $R_6$ and $R_7$ is independently hydrogen, alkyl or nitrogen protecting group, $R_{12}$ is a straight or branched chain alkyl, substituted alkyl, aryl, or substituted aryl, and each "n" is independently an integer from 0 to about 200; and introducing a phosphorus containing group at the secondary hydroxyl of Formula XIII to yield a compound of Formula V.

The present invention features a method for synthesizing a compound having Formula VIII:

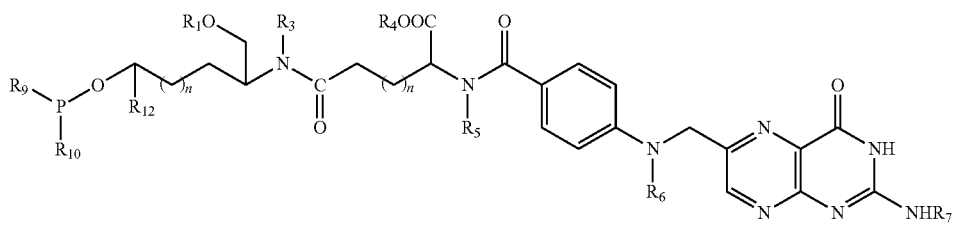

wherein each $R_1$ and $R_4$ is independently a protecting group or hydrogen, each $R_3$, $R_5$, $R_6$ and $R_7$ is independently hydrogen, alkyl or nitrogen protecting group, each "n" is independently an integer from 0 to about 200, each $R_9$ and $R_{10}$ is independently a nitrogen containing group, cyanoalkoxy, alkoxy, aryloxy, or alkyl group, and $R_{12}$ is a straight or branched chain alkyl, substituted alkyl, aryl, or substituted aryl, comprising; coupling a bis-hydroxy aminoalkyl derivative, for example D-threoninol, with a protected amino acid, for example glutamic acid, to yield a compound of Formula XIV;

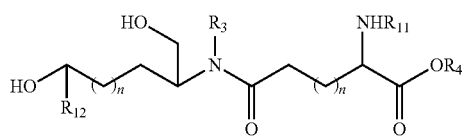

wherein $R_{11}$ is an amino protecting group, each "n" is independently an integer from 0 to about 200, $R_4$ is independently a protecting group, and $R_{12}$ is a straight or branched chain alkyl, substituted alkyl, aryl, or substituted aryl; introducing primary hydroxy protection $R_1$ followed by amino deprotection of $R_{11}$ of Formula XIV to yield a compound of Formula XV;

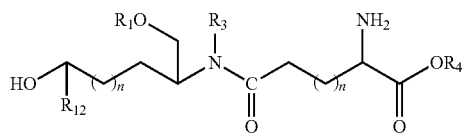

wherein each $R_1$ and $R_4$ is independently a protecting group or hydrogen, $R_{12}$ is a straight or branched chain alkyl, substituted alkyl, aryl, or substituted aryl, and each "n" is independently an integer from 0 to about 200; coupling the deprotected amine of Formula XV with an amino protected pteroic acid to yield a compound of Formula XVI;

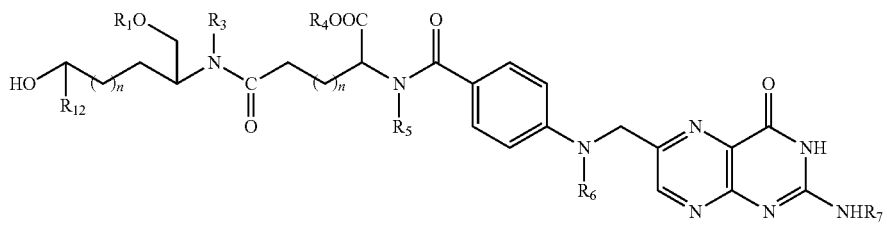

wherein each $R_1$ and $R_4$ is independently a protecting group or hydrogen, each $R_3$, $R_5$, $R_6$ and $R_7$ is independently hydrogen, alkyl or nitrogen protecting group, $R_{12}$ is a straight or branched chain alkyl, substituted alkyl, aryl, or substituted aryl, and each "n" is independently an integer from 0 to about 200; and introducing a phosphorus containing group at the secondary hydroxyl of Formula XVI to yield a compound of Formula VIII.

In one embodiment, $R_2$ of a compound of the invention comprises a phosphorus containing group.

In another embodiment, $R_2$ of a compound of the invention comprises a nucleoside, for example, a nucleoside with beneficial activity such as anticancer or antiviral activity.

In yet another embodiment, $R_2$ of a compound of the invention comprises a nucleotide, for example, a nucleotide with beneficial activity such as anticancer or antiviral activity.

In a further embodiment, $R_2$ of a compound of the invention comprises a small molecule, for example, a small molecule with beneficial activity such as anticancer or antiviral activity.

In another embodiment, $R_2$ of a compound of the invention comprises a nucleic acid, for example, a nucleic acid with beneficial activity such as anticancer or antiviral activity.

In one embodiment, $R_2$ of a compound of the invention comprises a solid support comprising a linker.

In another embodiment, a nucleoside ($R_2$) of the invention comprises a nucleoside with anticancer activity.

In another embodiment, a nucleoside ($R_2$) of the invention comprises a nucleoside with antiviral activity.

In another embodiment, the nucleoside ($R_2$) of the invention comprises fludarabine, lamivudine (3TC), 5-fluoro uridine, AZT, ara-adenosine, ara-adenosine monophosphate, a dideoxy nucleoside analog, carbodeoxyguanosine, ribavirin, fialuridine, lobucavir, a pyrophosphate nucleoside analog, an acyclic nucleoside analog, acyclovir, gangciclovir, penciclovir, famciclovir, an L-nucleoside analog, FTC, L-FMAU, L-ddC, L-FddC, L-d4C, L-Fd4C, an L-dideoxypurine nucleoside analog, cytallene, bis-POM PMEA (GS-840), BMS-200, 475, carbovir or abacavir.

In one embodiment, $R_{13}$ of a compound of the invention comprises an alkylamino or an alkoxy group, for example, —$CH_2O$— or —$CH(CH_2)CH_2O$—.

In another embodiment, $R_{12}$ of a compound of the invention is an alkylhyrdroxyl, for example, —(CH$_2$)—OH, where n comprises an integer from about 1 to about 10.

In another embodiment, L of Formula VI of the invention comprises serine, threonine, or a photolabile linkage.

In one embodiment, $R_9$ of a compound of the invention comprises a phosphorus protecting group, for example —OCH$_2$CH$_2$CN (oxyethylcyano).

In one embodiment, $R_{10}$ of a compound of the invention comprises a nitrogen containing group, for example, —N($R_{14}$) wherein $R_{14}$ is a straight or branched chain alkyl having from about 1 to about 10 carbons.

In another embodiment, $R_{10}$ of a compound of the invention comprises a heterocycloalkyl or heterocycloalkenyl ring containing from about 4 to about 7 atoms, and having from about 1 to about 3 heteroatoms comprising oxygen, nitrogen, or sulfur.

In another embodiment, $R_1$ of a compound of the invention comprises an acid labile protecting group, such as a trityl or substituted trityl group, for example, a dimethoxytrityl or mono-methoxytrityl group.

In another embodiment, $R_4$ of a compound of the invention comprises a tert-butyl, Fm (fluorenyl-methoxy), or allyl group.

In one embodiment, $R_6$ of a compound of the invention comprises a TFA (trifluoracetyl) group.

In another embodiment, $R_3$, $R_5$, $R_7$ and $R_8$ of a compound of the invention are independently hydrogen.

In one embodiment, $R_7$ of a compound of the invention is independently isobutyryl, dimethylformamide, or hydrogen.

In another embodiment, $R_{12}$ of a compound of the invention comprises a methyl group or ethyl group.

In one embodiment, a nucleic acid of the invention comprises an enzymatic nucleic acid, for example a hammerhead, Inozyme, DNAzyme, G-cleaver, Zinzyme, Amberzyme, or allozyme.

In another embodiment, a nucleic acid of the invention comprises an antisense nucleic acid, 2-5A nucleic acid chimera, or decoy nucleic acid.

In another embodiment, the solid support having a linker of the invention comprises a structure of Formula XVII:

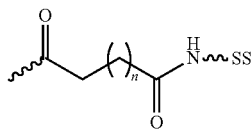

wherein SS is a solid support, and each "n" is independently an integer from about 1 to about 200.

In another embodiment, the solid support of the instant invention is controlled pore glass (CPG) or polystyrene, and can be used in the synthesis of a nucleic acid.

In one embodiment, the invention features a pharmaceutical composition comprising a compound of the invention and a pharmaceutically acceptable carrier.

In another embodiment, the invention features a method of treating a cancer patient, comprising contacting cells of the patient with a pharmaceutical composition of the invention under conditions suitable for the treatment. This treatment can comprise the use of one or more other drug therapies under conditions suitable for the treatment. The cancers contemplated by the instant invention include but are not limited to breast cancer, lung cancer, colorectal cancer, brain cancer, esophageal cancer, stomach cancer, bladder cancer, pancreatic cancer, cervical cancer, head and neck cancer, ovarian cancer, melanoma, lymphoma, glioma, or multidrug resistant cancers.

In one embodiment, the invention features a method of treating a patient infected with a virus, comprising contacting cells of the patient with a pharmaceutical composition of the invention, under conditions suitable for the treatment. This treatment can comprise the use of one or more other drug therapies under conditions suitable for the treatment. The viruses contemplated by the instant invention include but are not limited to HIV, HBV, HCV, CMV, RSV, HSV, poliovirus, influenza, rhinovirus, west nile virus, Ebola virus, foot and mouth virus, and papilloma virus.

In one embodiment, the invention features a kit for detecting the presence of a nucleic acid molecule or other target molecule in a sample, for example, a gene in a cancer cell, comprising a compound of the instant invention.

In one embodiment, the invention features a kit for detecting the presence of a nucleic acid molecule, or other target molecule in a sample, for example, a gene in a virus-infected cell, comprising a compound of the instant invention.

In another embodiment, the invention features a compound of the instant invention comprising a modified phosphate group, for example, a phosphoramidite, phosphodiester, phosphoramidate, phosphorothioate, phosphorodithioate, alkylphosphonate, arylphosphonate, monophosphate, diphosphate, triphosphate, or pyrophosphate.

In one embodiment, the invention features a method for synthesizing a compound having Formula XVIII:

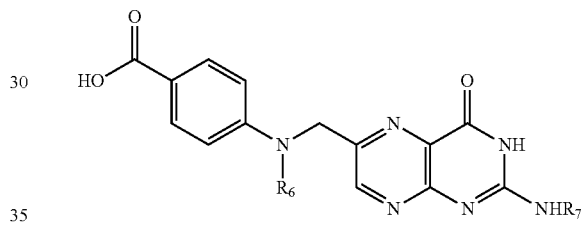

wherein each $R_6$ and $R_7$ is independently hydrogen, alkyl or nitrogen protecting group, comprising: reacting folic acid with a carboxypeptidase to yield a compound of Formula XIX;

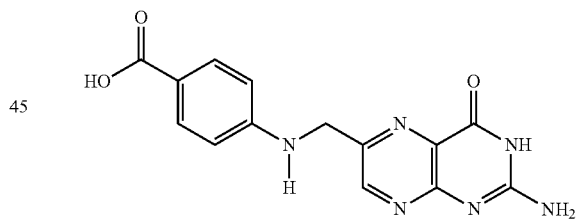

introducing a protecting group $R_6$ on the secondary amine of Formula XIX to yield a compound of Formula XX;

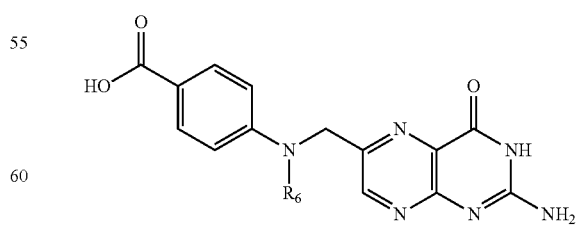

wherein $R_6$ is a nitrogen protecting group; and introducing a protecting group $R_7$ on the primary amine of Formula XX to yield a compound of Formula XVIII.

In another embodiment, the amino protected pteroic acid of the invention is a compound of Formula XVIII.

In one embodiment, the invention encompasses a compound of Formula I having Formula XXI:

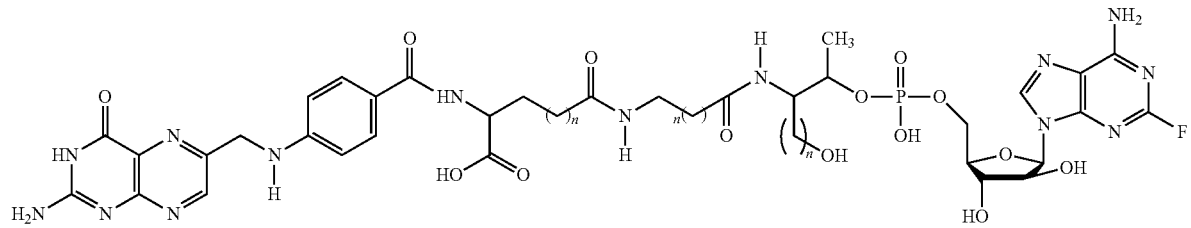

wherein each "n" is independently an integer from 0 to about 200.

In another embodiment, the invention encompasses a compound of Formula VII having Formula XXII:

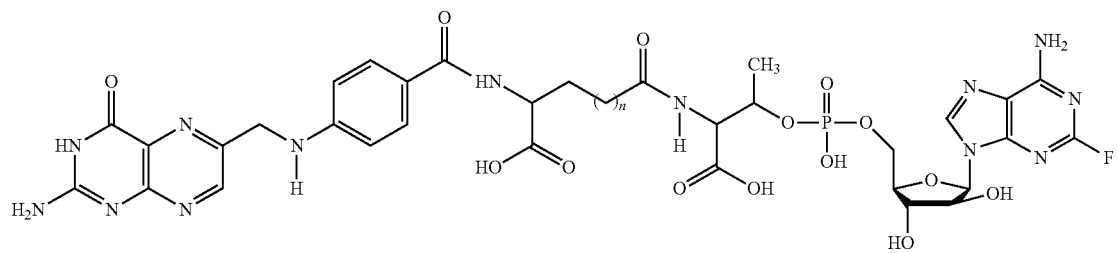

wherein each "n" is independently an integer from 0 to about 200.

In another embodiment, the invention encompasses a compound of Formula IV having Formula XXIII:

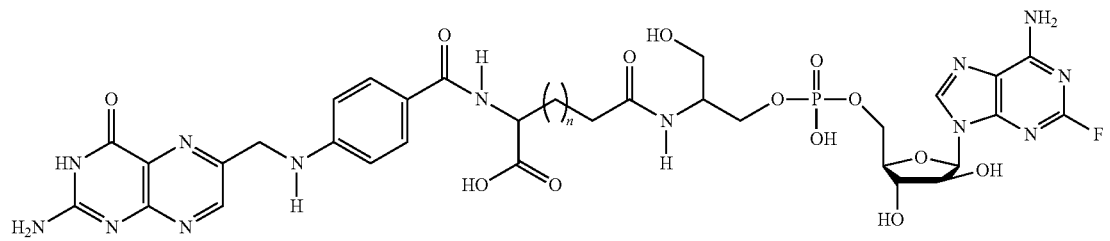

wherein "n" is an integer from 0 to about 200.

In another embodiment, the invention encompasses a compound of Formula IV having Formula XXIV:

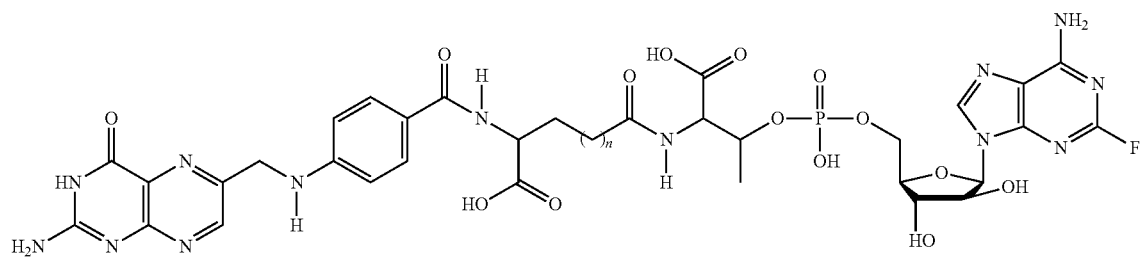

wherein "n" is an integer from 0 to about 200.

In another embodiment, the invention features a compound having Formula XXV:

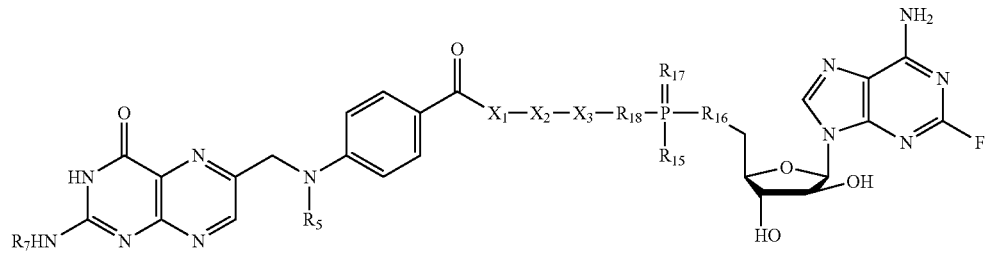

wherein each $R_5$ and $R_7$ is independently hydrogen, alkyl or a nitrogen protecting group, each $R_{15}$, $R_{16}$, $R_{17}$, and $R_{18}$ is independently O, S, alkyl, substituted alkyl, aryl, substituted aryl, or halogen, $X_1$ is —CH($X_{1'}$) or a group of Formula XXVI:

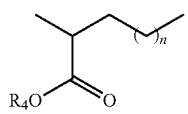

wherein $R_4$ is a protecting group and "n" is an integer from 0 to about 200;
$X_{1'}$ is the protected or unprotected side chain of a naturally occurring or non-naturally-occurring amino acid, $X_2$ is amide, alkyl, or carbonyl containing linker or a bond, and $X_3$ is a degradable linker which is optionally absent.

In another embodiment, the $X_3$ group of Formula XXV comprises a group of Formula XXVI:

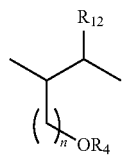

wherein $R_4$ is hydrogen or a protecting group, "n" is an integer from 0 to about 200 and $R_{12}$ is a straight or branched chain alkyl, substituted alkyl, aryl, or substituted aryl.

In yet another embodiment, $R_4$ of Formula XXVI is hydrogen and $R_{12}$ is methyl or hydrogen.

In still another embodiment, the invention features a compound having Formula XXVII:

wherein "n" is an integer from about 0 to about 20, $R_4$ is H or a cationic salt, and $R_{24}$ is a sulfur containing leaving group, for example a group comprising:

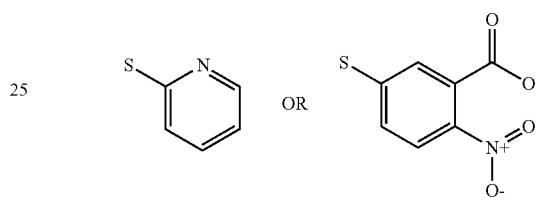

In another embodiment, the invention features a method for synthesizing a compound having Formula XXVII comprising:

(a) selective tritylation of the thiol of cysteamine under conditions suitable to yield a compound having Formula XXVIII:

wherein "n" is an integer from about 0 to about 20 and $R_{19}$ is a thiol protecting group;

(b) peptide coupling of the product of (a) with a compound having Formula XXIX:

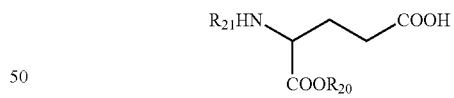

wherein $R_{20}$ is a carboxylic acid protecting group and $R_{21}$ is an amino protecting group, under conditions suitable to yield a compound having Formula XXX:

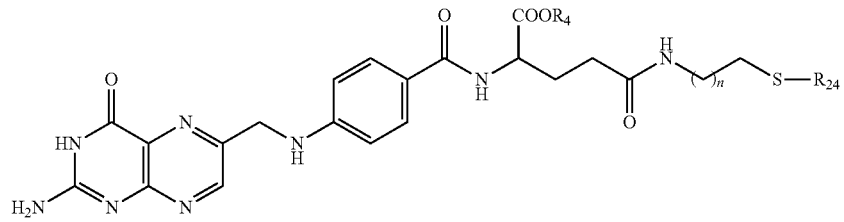

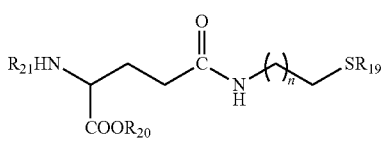

wherein "n" is an integer from about 0 to about 20, $R_{19}$ is a thiol protecting group, $R_{20}$ is a carboxylic acid protecting group and $R_{21}$ is an amino protecting group;

(c) removing the amino protecting group $R_{21}$ of the product of (b) under conditions suitable to yield a compound having Formula XXXI:

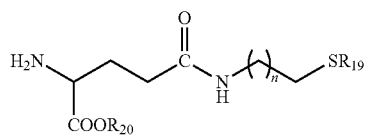

wherein "n" is an integer from about 0 to about 20 and $R_{19}$ and $R_{20}$ are as described in (b);

(d) condensation of the product of (c) with a compound having Formula XXXII:

wherein $R_{22}$ is an amino protecting group, under conditions suitable to yield a compound having Formula XXXIII:

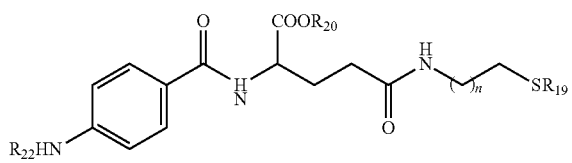

wherein "n" is an integer from about 0 to about 20 and $R_{19}$ and $R_{20}$ are as described in (b) and $R_{22}$ is as described in (d);

(e) selective cleavage of $R_{22}$ from the product of (d) under conditions suitable to yield a compound having Formula XXXIV:

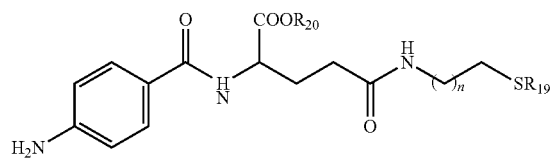

wherein "n" is an integer from about 0 to about 20 and $R_{19}$ and $R_{20}$ are as described in (b);

(f) coupling the product of (e) with a compound having Formula XXXV:

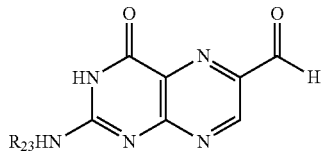

wherein $R_{23}$ is an amino protecting group under conditions suitable to yield a compound having Formula XXXVI:

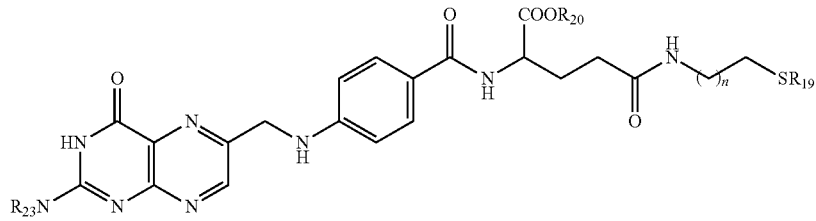

wherein $R_{23}$ is an amino protecting group, "n" is an integer from about 0 to about 20 and $R_{19}$ and $R_{20}$ are as described in (b);

(g) deprotecting the product of (f) under conditions suitable to yield a compound having Formula XVIII.

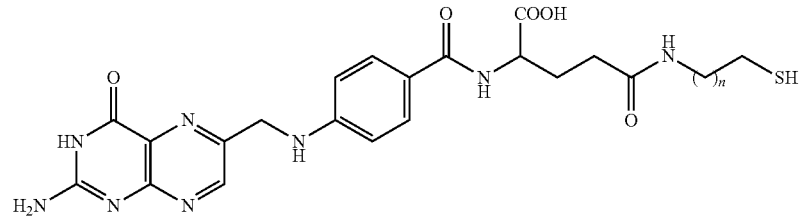

wherein "n" is an integer from about 0 to about 20; and (h) introducing a disulphide-based leaving group to the product of (g) under conditions suitable to yield a compound having Formula XXVII.

In one embodiment, the invention features a compound having Formula XXIX:

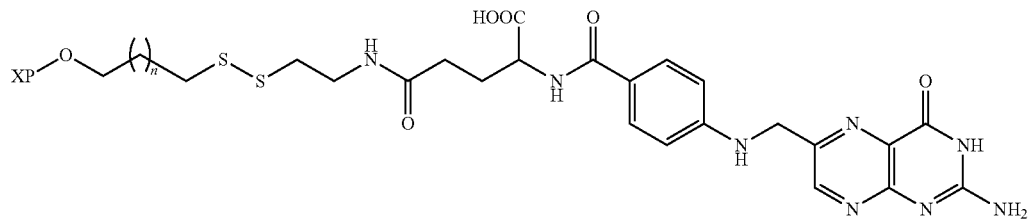

wherein "n" is an integer from about 0 to about 20, X is a nucleic acid, polynucleotide, or oligonucleotide, and P is a phosphorus containing group.

In another embodiment, the invention features a method for synthesizing a compound having Formula XXIX, comprising:

(a) Coupling a thiol containing linker to a nucleic acid, polynucleotide or oligonucleotide under conditions suitable to yield a compound having Formula XXX:

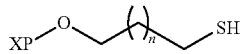

wherein "n" is an integer from about 0 to about 20, X is a nucleic acid, polynucleotide, or oligonucleotide, and P is a phosphorus containing group; and (b) coupling the product of (a) with a compound having Formula XXVII under conditions suitable to yield a compound having Formula XXIX.

In another embodiment, the thiol containing linker of the invention is a compound having Formula XXXI:

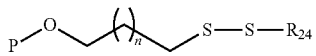

wherein "n" is an integer from about 0 to about 20, P is a phosphorus containing group, for example a phosphine, phosphite, or phosphate, and $R_{24}$ is any alkyl, substituted alkyl, alkoxy, aryl, substituted aryl, alkenyl, substituted alkenyl, alkynyl, or substituted alkynyl group with or without additional protecting groups.

In another embodiment, the conditions suitable to yield a compound having Formula XXX comprises reduction, for example using dithiothreitol (DTT) or any equivalent disulphide reducing agent, of the disulfide bond of a compound having Formula XXXII:

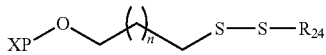

wherein "n" is an integer from about 0 to about 20, X is a nucleic acid, polynucleotide, or oligonucleotide, P is a phosphorus containing group, and $R_{24}$ is any alkyl, substituted alkyl, alkoxy, aryl, substituted aryl, alkenyl, substituted alkenyl, alkynyl, or substituted alkynyl group with or without additional protecting groups.

In one embodiment, the nucleic acid conjugates of the instant invention are assembled post synthetically, for example, following solid phase oligonucleotide synthesis.

The present invention provides compositions and conjugates comprising nucleosidic and non-nucleosidic folate derivatives. The present invention also provides nucleic acid folate derivatives including RNA, DNA, and PNA based conjugates. The attachment of folate compounds of the invention to nucleosides, nucleotides, non-nucleosides, and nucleic acid molecules is provided at any position within the molecule, for example, at internucleotide linkages, nucleosidic sugar hydroxyl groups such as 5', 3', and 2'-hydroxyls, and/or at nucleobase positions such as amino and carbonyl groups.

The exemplary folate conjugates of the invention are described as compounds of Formulae I-XXV, however, other folate and antifolate derivatives are provided by the invention, including various folate analogs of the compounds of Formulae I-XXV, including dihydrofloates, tetrahydrofolates, tetrahydrorpterins, folinic acid, pteropolyglutamic acid, 1-deza, 3-deaza, 5-deaza, 8-deaza, 10-deaza, 1,5-deaza, 5,10 dideaza, 8,10-dideaza, and 5,8-dideaza folates, antifolates, and pteroic acids. As used herein, the term "folate" is meant to refer to folate and folate derivatives, including pteroic acid derivatives and analogs.

The present invention features compositions and conjugates to facilitate delivery of molecules into a biological system such as cells. The folate conjugates provided by the instant invention can impart therapeutic activity by transferring therapeutic compounds across cellular membranes. The present invention encompasses the design and synthesis of novel agents for the delivery of molecules, including but not limited to small molecules, lipids, nucleosides, nucleotides, nucleic acids, negatively charged polymers and other polymers, for example proteins, peptides, carbohydrates, or polyamines. In general, the transporters described are designed to be used either individually or as part of a multi-component system. The compounds of the invention generally shown in Formulae I-XXV, are expected to improve delivery of molecules into a number of cell types originating from different tissues, in the presence or absence of serum.

In one embodiment, the present invention features molecules, compositions and conjugates of molecules, for example, non-nucleosidic small molecules, nucleosides, nucleotides, and nucleic acids, such as enzymatic nucleic acid molecules, antisense nucleic acids, 2-5A antisense chimeras, triplex DNA, decoy RNA, aptamers, and antisense nucleic acids containing RNA cleaving chemical groups.

In another embodiment, the present invention features methods to modulate gene expression, for example, genes involved in the progression and/or maintenance of cancer or in a viral infection. For example, in one embodiment, the invention features the use of one or more of the nucleic acid-based molecules and methods independently or in combination to inhibit the expression of the gene(s) encoding proteins associated with cancerous conditions, for example breast cancer, lung cancer, colorectal cancer, brain cancer, esophageal cancer, stomach cancer, bladder cancer, pancreatic cancer, cervical cancer, head and neck cancer, ovarian cancer, melanoma, lymphoma, glioma, or multidrug resistant cancer associated genes.

In another embodiment, the invention features the use of one or more of the nucleic acid-based molecules and methods independently or in combination to inhibit the expression of the gene(s) encoding viral proteins, for example HIV, HBV, HCV, CMV, RSV, HSV, poliovirus, influenza, rhinovirus, west nile virus, Ebola virus, foot and mouth virus, and papilloma virus associated genes.

In one embodiment, the invention features the use of an enzymatic nucleic acid molecule folate conjugate, preferably in the hammerhead, NCH, G-cleaver, amberzyme, zinzyme and/or DNAzyme motif, to inhibit the expression of cancer and virus associated genes.

In another embodiment, the invention features the use of an enzymatic nucleic acid molecule as a folate conjugate. These enzymatic nucleic acids can catalyze the hydrolysis of RNA phosphodiester bonds in trans (and thus can cleave other RNA molecules) under physiological conditions. Table I summarizes some of the characteristics of these enzymatic nucleic acids. Without being bound by any particular theory, in general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA destroys its ability to direct synthesis of an encoded protein. After an enzymatic nucleic acid has bound and cleaved its RNA target, it is released from that RNA to search for another target and can repeatedly bind and cleave new targets. Thus, a single enzymatic nucleic acid molecule is able to cleave many molecules of target RNA. In addition, the enzymatic nucleic acid is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of an enzymatic nucleic acid.

In one embodiment of the invention described herein, the enzymatic nucleic acid molecule component of the folate conjugate is formed in a hammerhead or hairpin motif, but can also be formed in the motif of a hepatitis delta virus, group I intron, group II intron or RNase P RNA (in association with an RNA guide sequence), Neurospora VS RNA, DNAzymes, NCH cleaving motifs, or G-cleavers. Examples of such hammerhead motifs are described by Dreyfus, supra, Rossi et al., 1992, AIDS Research and Human Retroviruses 8, 183; of hairpin motifs by Hampel et al., EP0360257, Hampel and Tritz, 1989 Biochemistry 28, 4929, Feldstein et al., 1989, Gene 82, 53, Haseloff and Gerlach, 1989, Gene, 82, 43, and Hampel et al., 1990 Nucleic Acids Res. 18, 299; Chowrira & McSwiggen, U.S. Pat. No. 5,631,359; of the hepatitis delta virus motif is described by Perrotta and Been, 1992 Biochemistry 31, 16; of the RNase P motif by Guerrier-Takada et al., 1983 Cell 35, 849; Forster and Altman, 1990, Science 249, 783; Li and Altman, 1996, Nucleic Acids Res. 24, 835; Neurospora VS RNA ribozyme motif is described by Collins (Saville and Collins, 1990 Cell 61, 685-696; Saville and Collins, 1991 Proc. Natl. Acad. Sci. USA 88, 8826-8830; Collins and Olive, 1993 Biochemistry 32, 2795-2799; Guo and Collins, 1995, EMBO. J. 14, 363); Group II introns are described by Griffin et al., 1995, Chem. Biol. 2, 761; Michels and Pyle, 1995, Biochemistry 34, 2965; Pyle et al., International PCT Publication No. WO 96/22689; of the Group I intron by Cech et al., U.S. Pat. No. 4,987,071 and of DNAzymes by Usman et al., International PCT Publication No. WO 95/11304; Chartrand et al., 1995, NAR 23, 4092; Breaker et al., 1995, Chem. Bio. 2, 655; Santoro et al., 1997, PNAS 94, 4262, and Beigelman et al., International PCT publication No. WO 99/55857. NCH cleaving motifs are described in Ludwig & Sproat, International PCT Publication No. WO 98/58058; and G-cleavers are described in Kore et al., 1998, Nucleic Acids Research 26, 4116-4120 and Eckstein et al., International PCT Publication No. WO 99/16871. Additional motifs such as the Aptazyme (Breaker et al., WO 98/43993), Amberzyme (Class I motif; FIG. 3; Beigelman et al., U.S. Ser. No. 09/301,511) and Zinzyme (FIG. 4) (Beigelman et al., U.S. Ser. No. 09/301,511), all incorporated by reference herein including drawings, can also be used in the present invention. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule (Cech et al., U.S. Pat. No. 4,987,071).

In one embodiment of the present invention, a nucleic acid molecule component of a conjugate of the instant invention can be between 12 and 100 nucleotides in length. For example, enzymatic nucleic acid molecules of the invention are preferably between 15 and 50 nucleotides in length, more preferably between 25 and 40 nucleotides in length, e.g., 34, 36, or 38 nucleotides in length (for example see Jarvis et al., 1996, J. Biol. Chem., 271, 29107-29112). Exemplary DNAzymes of the invention are preferably between 15 and 40 nucleotides in length, more preferably between 25 and 35 nucleotides in length, e.g., 29, 30, 31, or 32 nucleotides in length (see for example Santoro et al., 1998, Biochemistry, 37, 13330-13342; Chartrand et al., 1995, Nucleic Acids Research, 23, 4092-4096). Exemplary antisense molecules of the invention are preferably between 15 and 75 nucleotides in length, more preferably between 20 and 35 nucleotides in length, e.g., 25, 26, 27, or 28 nucleotides in length (see, for example, Woolf et al., 1992, PNAS., 89, 7305-7309; Milner et al., 1997, Nature Biotechnology, 15, 537-541). Exemplary triplex forming oligonucleotide molecules of the invention are preferably between 10 and 40 nucleotides in length, more preferably between 12 and 25 nucleotides in length, e.g., 18, 19, 20, or 21 nucleotides in length (see for example Maher et al., 1990, Biochemistry, 29, 8820-8826; Strobel and Dervan, 1990, Science, 249, 73-75). Those skilled in the art will recognize that all that is required is for the nucleic acid molecule to be of sufficient length and suitable conformation for the nucleic acid molecule to catalyze a reaction contemplated herein. The length of the nucleic acid molecules described and exemplified herein are not not limiting within the general size ranges stated.

The folate conjugates of the invention are added directly, or can be complexed with cationic lipids, packaged within liposomes, or otherwise delivered to target cells or tissues. The conjugates and/or conjugate complexes can be locally administered to relevant tissues ex vivo, or in vivo through injection or infusion pump, with or without their incorporation in biopolymers. The compositions and conjugates of the instant invention, individually, or in combination or in conjunction with other drugs, can be used to treat diseases or conditions discussed above. For example, to treat a disease or condition associated with the levels of a pathogenic protein, the patient can be treated, or other appropriate cells can be treated, as is evident to those skilled in the art, individually or in combination with one or more drugs under conditions suitable for the treatment.

In a further embodiment, the described molecules can be used in combination with other known treatments to treat conditions or diseases discussed above. For example, the described molecules can be used in combination with one or more known therapeutic agents to treat breast, lung, prostate, colorectal, brain, esophageal, bladder, pancreatic, cervical, head and neck, and ovarian cancer, melanoma, lymphoma, glioma, multidrug resistant cancers, and/or HIV, HBV, HCV, CMV, RSV, HSV, poliovirus, influenza, rhinovirus, west nile virus, Ebola virus, foot and mouth virus, and papilloma virus infection.

Included in another embodiment are a series of multi-domain cellular transport vehicles (MCTV) including one or more compounds of Formula I-XXV that enhance the cellular uptake and transmembrane permeability of negatively charged molecules in a variety of cell types. The compounds of the invention are used either alone or in combination with other compounds with a neutral or a negative charge including but not limited to neutral lipid and/or targeting components, to improve the effectiveness of the formulation or conjugate in delivering and targeting the predetermined compound or molecule to cells. Another embodiment of the invention encompasses the utility of these compounds for increasing the transport of other impermeable and/or lipophilic compounds into cells. Targeting components include ligands for cell surface receptors including, peptides and proteins, glycolipids, lipids, carbohydrates, and their synthetic variants, for example folate receptors.

In another embodiment, the compounds of the invention are provided as a surface component of a lipid aggregate, such as a liposome encapsulated with the predetermined molecule to be delivered. Liposomes, which can be unilamellar or multilamellar, can introduce encapsulated material into a cell by different mechanisms. For example, the liposome can directly introduce its encapsulated material into the cell cytoplasm by fusing with the cell membrane. Alternatively, the liposome can be compartmentalized into an acidic vacuole (i.e., an endosome) and its contents released from the liposome and out of the acidic vacuole into the cellular cytoplasm.

In one embodiment the invention features a lipid aggregate formulation of Formulae I-XXV, including phosphatidylcholine (of varying chain length; e.g., egg yolk phosphatidylcholine), cholesterol, a cationic lipid, and 1,2-distearoyl-sn-glycero-3-phosphoethanolamine-polythyleneglycol-2000 (DSPE-PEG2000). The cationic lipid component of this lipid aggregate can be any cationic lipid known in the art such as dioleoyl 1,2,-diacyl-3-trimethylammonium-propane (DOTAP). In another embodiment this cationic lipid aggregate comprises a covalently bound compound described in any of the Formula I-XXV.

In another embodiment, polyethylene glycol (PEG) is covalently attached to the compounds of the present invention. The attached PEG can be any molecular weight but is preferably between 2000-50,000 daltons.

The compounds and methods of the present invention are useful for introducing nucleotides, nucleosides, nucleic acid molecules, lipids, peptides, proteins, and/or non-nucleosidic small molecules into a cell. For example, the invention can be used for nucleotide, nucleoside, nucleic acid, lipids, peptides, proteins, and/or non-nucleosidic small molecule delivery where the corresponding target site of action exists intracellularly.

In one embodiment, the compounds of the instant invention provide conjugates of molecules that can interact with folate receptors, such as high affinity folate receptors, and provide a number of features that allow the efficient delivery and subsequent release of conjugated compounds across biological membranes. The compounds utilize chemical linkages between the folate and the compound to be delivered of length that can interact preferentially with folate receptors. Furthermore, the chemical linkages between the folate and the compound to be delivered can be designed as degradable linkages, for example by utilizing a phosphate linkage that is proximal to a nucleophile, such as a hydroxyl group. Deprotonation of the hydroxyl group or an equivalent group, as a result of pH or interaction with a nuclease, can result in nucleophilic attack of the phosphate resulting in a cyclic phosphate intermediate that can be hydrolyzed. This cleavage mechanism is analogous RNA cleavage in the presence of a base or RNA nuclease. Alternately, other degradable linkages can be selected that respond to various factors such as UV irradiation, cellular nucleases, pH, temperature etc. The use of degradable linkages allows the delivered compound to be released in a predetermined system, for example in the cytoplasm of a cell, or in a particular cellular organelle.

The present invention also provides folate derived phosphoramidites that are readily conjugated to compounds and molecules of interest. Phosphoramidite compounds of the invention permit the direct attachment of folate conjugates to molecules of interest without the need for using nucleic acid phosphoramidite species as scaffolds. As such, the used of phosphoramidite chemistry can be used directly in coupling the folate conjugates to a compound of interest, without the need for other condensation reactions, such as condensation of the folate to an amino group on the nucleic acid, for example at the N6 position of adenosine or a 2'-deoxy-2'-amino function. Additionally, compounds of the invention can be used to introduce non-nucleic acid based folate conjugated linkages into oligonucleotides that can provide more efficient coupling during oligonucleotide synthesis than the use of nucleic acid-based folate phosphoramidites. This improved coupling can take into account improved steric considerations of abasic or non-nucleosidic scaffolds bearing pendant alkyl linkages.

Compounds of the invention utilizing triphosphate groups can be utilized in the enzymatic incorporation of conjugate molecules into oligonucleotides. Such enzymatic incorporation is useful when conjugates are used in post-synthetic enzymatic conjugation or selection reactions, (see for example Matulic-Adamic et al., 2000, *Bioorg. Med. Chem. Lett.*, 10, 1299-1302; Lee et al., 2001, *NAR.*, 29, 1565-1573; Joyce, 1989, *Gene*, 82, 83-87; Beaudry et al., 1992, *Science* 257, 635-641; Joyce, 1992, *Scientific American* 267, 90-97; Breaker et al., 1994, *TIBTECH* 12, 268; Bartel et al., 1993, *Science* 261:1411-1418; Szostak, 1993, *TIBS* 17, 89-93; Kumar et al., 1995, *FASEB* 1, 9, 1183; Breaker, 1996, *Curr. Op. Biotech.*, 7, 442; Santoro et al., 1997, *Proc. Natl. Acad. Sci.*, 94, 4262; Tang et al., 1997, *RNA* 3, 914; Nakamaye & Eckstein, 1994, supra; Long & Uhlenbeck, 1994, supra; Ishizaka et al., 1995, supra; Vaish et al., 1997, *Biochemistry* 36, 6495; Kuwabara et al., 2000, *Curr. Opin. Chem. Biol.*, 4, 669).

Compounds of the invention can be used to detect the presence of a target molecule in a biological system, such as tissue, cell or cell lysate. Examples of target molecules include nucleic acids, proteins, peptides, antibodies, polysaccharides, lipids, hormones, sugars, metals, microbial or cellular metabolites, analytes, pharmaceuticals, and other organic and inorganic molecules or other biomolecules in a sample. The compounds of the instant invention can be conjugated to a predetermined compound or molecule that is capable of interacting with the target molecule in the system and providing a detectable signal or response. Various compounds and molecules known in the art that can be used in these applications include but are not limited to antibodies, labeled antibodies, allozymes, aptamers, labeled nucleic acid probes, molecular beacons, fluorescent molecules, radioisotopes, polysaccharides, and any other compound capable of interacting with the target molecule and generating a detectable signal upon target interaction. For example, such compounds are described in Application entitled "NUCLEIC ACID SENSOR MOLECULES" filed on Mar. 6, 2001 Ser. No. 09/800,594 with inventors Nassim Usman and James A. McSwiggen, which is incorporated by reference in its entirety, including the drawings.

The term "target molecule" as used herein, refers to nucleic acid molecules, proteins, peptides, antibodies, polysaccharides, lipids, sugars, metals, microbial or cellular metabolites, analytes, pharmaceuticals, and other organic and inorganic molecules that are present in a system.

By "inhibit" or "down-regulate" it is meant that the expression of the gene, or level of RNAs or equivalent RNAs encoding one or more protein subunits, or activity of one or more protein subunits, such as pathogenic protein, viral protein or cancer related protein subunit(s), is reduced below that observed in the absence of the compounds or combination of compounds of the invention. In one embodiment, inhibition or down-regulation with an enzymatic nucleic acid molecule preferably is below that level observed in the presence of an enzymatically inactive or attenuated molecule that is able to bind to the same site on the target RNA, but is unable to cleave that RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of viral or oncogenic RNA, protein, or protein subunits with a compound of the instant invention is greater in the presence of the compound than in its absence.

By "up-regulate" is meant that the expression of the gene, or level of RNAs or equivalent RNAs encoding one or more protein subunits, or activity of one or more protein subunits, such as viral or oncogenic protein subunit(s), is greater than that observed in the absence of the compounds or combination of compounds of the invention. For example, the expression of a gene, such as a viral or cancer related gene, can be increased in order to treat, prevent, ameliorate, or modulate a pathological condition caused or exacerbated by an absence or low level of gene expression.

By "modulate" is meant that the expression of the gene, or level of RNAs or equivalent RNAs encoding one or more protein subunits, or activity of one or more protein subunit(s) of a protein, for example a viral or cancer related protein is up-regulated or down-regulated, such that the expression, level, or activity is greater than or less than that observed in the absence of the compounds or combination of compounds of the invention.

The term "enzymatic nucleic acid molecule" as used herein refers to a nucleic acid molecule which has complementarity in a substrate binding region to a specified gene target, and also has an enzymatic activity which is active to specifically cleave target RNA. That is, the enzymatic nucleic acid molecule is able to intermolecularly cleave RNA and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50-75% can also be useful in this invention (see for example Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030).

The term "nucleic acid molecule" as used herein, refers to a molecule having nucleotides. The nucleic acid can be single, double, or multiple stranded and can comprise modified or unmodified nucleotides or non-nucleotides or various mixtures and combinations thereof.

The term "enzymatic portion" or "catalytic domain" as used herein refers to that portion/region of the enzymatic nucleic acid molecule essential for cleavage of a nucleic acid substrate (for example see FIG. 1).

The term "substrate binding arm" or "substrate binding domain" as used herein refers to that portion/region of a enzymatic nucleic acid which is able to interact, for example via complementarity (i.e., able to base-pair with), with a portion of its substrate. Preferably, such complementarity is 100%, but can be less if desired. For example, as few as 10 bases out of 14 can be base-paired (see for example Werner and Uhlenbeck, 1995, Nucleic Acids Research, 23, 2092-2096; Hammann et al., 1999, Antisense and Nucleic Acid Drug Dev., 9, 25-31). Examples of such arms are shown generally in FIGS. 1-4. That is, these arms contain sequences within a enzymatic nucleic acid which are intended to bring enzymatic nucleic acid and target RNA together through complementary base-pairing interactions. The enzymatic nucleic acid of the invention can have binding arms that are contiguous or non-contiguous and can be of varying lengths. The length of the binding arm(s) are preferably greater than or equal to four nucleotides and of sufficient length to stably interact with the target RNA; preferably 12-100 nucleotides; more preferably 14-24 nucleotides long (see for example Werner and Uhlenbeck, supra; Hamman et al., supra; Hampel et al., EP0360257; Berzal-Herrance et al., 1993, EMBO J., 12, 2567-73). If two binding arms are chosen, the design is such that the length of the binding arms are symmetrical (i.e., each of the binding arms is of the same length; e.g., five and five nucleotides, or six and six nucleotides, or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

The term "Inozyme" or "NCH" motif as used herein, refers to an enzymatic nucleic acid molecule comprising a motif as is generally described as NCH Rz in FIG. 1. Inozymes possess endonuclease activity to cleave RNA substrates having a cleavage triplet NCH/, where N is a nucleotide, C is cytidine and H is adenosine, uridine or cytidine, and / represents the cleavage site. H is used interchangeably with X. Inozymes can also possess endonuclease activity to cleave RNA substrates having a cleavage triplet NCN/, where N is a nucleotide, C is cytidine, and / represents the cleavage site. "I" in FIG. 2 represents an Inosine nucleotide, preferably a ribo-Inosine or xylo-Inosine nucleoside.

The term "G-cleaver" motif as used herein, refers to an enzymatic nucleic acid molecule comprising a motif as is generally described as G-cleaver Rz in FIG. 1. G-cleavers possess endonuclease activity to cleave RNA substrates having a cleavage triplet NYN/, where N is a nucleotide, Y is uridine or cytidine and / represents the cleavage site. G-cleavers can be chemically modified as is generally shown in FIG. 2.

The term "amberzyme" motif as used herein, refers to an enzymatic nucleic acid molecule comprising a motif as is generally described in FIG. 2. Amberzymes possess endonuclease activity to cleave RNA substrates having a cleavage triplet NG/N, where N is a nucleotide, G is guanosine, and / represents the cleavage site. Amberzymes can be chemically modified to increase nuclease stability through substitutions as are generally shown in FIG. 3. In addition, differing nucleoside and/or non-nucleoside linkers can be used to substitute the 5'-gaaa-3' loops shown in the figure. Amberzymes represent a non-limiting example of an enzymatic nucleic acid molecule that does not require a ribonucleotide (2'-OH) group within its own nucleic acid sequence for activity.

The term "zinzyme" motif as used herein, refers to an enzymatic nucleic acid molecule comprising a motif as is generally described in FIG. 3. Zinzymes possess endonuclease activity to cleave RNA substrates having a cleavage triplet including but not limited to YG/Y; where Y is uridine or cytidine, and G is guanosine and / represents the cleavage site. Zinzymes can be chemically modified to increase nuclease stability through substitutions as are generally shown in FIG. 3, including substituting 2'-O-methyl guanosine nucleotides for guanosine nucleotides. In addition, differing nucleotide and/or non-nucleotide linkers can be used to substitute the 5'-gaaa-2' loop shown in the figure. Zinzymes represent a non-limiting example of an enzymatic nucleic acid molecule that does not require a ribonucleotide (2'-OH) group within its own nucleic acid sequence for activity.

The term 'DNAzyme' as used herein, refers to an enzymatic nucleic acid molecule that does not require the presence of a 2'-OH group for its activity. In particular embodiments the enzymatic nucleic acid molecule can have an attached linker(s) or other attached or associated groups, moieties, or chains containing one or more nucleotides with 2'-OH groups. DNAzymes can be synthesized chemically or expressed endogenously in vivo, by means of a single stranded DNA vector or equivalent thereof. An example of a DNAzyme is shown in FIG. 4 and is generally reviewed in Usman et al., International PCT Publication No. WO 95/11304; Chartrand et al., 1995, NAR 23, 4092; Breaker et al., 1995, Chem. Bio. 2, 655; Santoro et al., 1997, PNAS 94, 4262; Breaker, 1999, Nature Biotechnology, 17, 422-423; and Santoro et. al., 2000, J. Am. Chem. Soc., 122, 2433-39. Additional DNAzyme motifs can be selected for using techniques similar to those described in these references, and hence, are within the scope of the present invention.

The term "sufficient length" as used herein, refers to an oligonucleotide of length great enough to provide the intended function under the expected condition, i.e., greater than or equal to 3 nucleotides. For example, for binding arms of enzymatic nucleic acid "sufficient length" means that the binding arm sequence is long enough to provide stable binding to a target site under the expected binding conditions. Preferably, the binding arms are not so long as to prevent useful turnover of the nucleic acid molecule.

The term "stably interact" as used herein, refers to interaction of the oligonucleotides with target nucleic acid (e.g., by forming hydrogen bonds with complementary nucleotides in the target under physiological conditions) that is sufficient to the intended purpose (e.g., cleavage of target RNA by an enzyme).

The term "homology" as used herein, refers to the nucleotide sequence of two or more nucleic acid molecules is partially or completely identical.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

The term "RNase H activating region" as used herein, refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see for example Arrow et al., U.S. Pat. No. 5,849,902; Arrow et al., U.S. Pat. No. 5,989, 912). The RNase H enzyme binds to the nucleic acid molecule-target RNA complex and cleaves the target RNA sequence. The RNase H activating region comprises, for example, phosphodiester, phosphorothioate (preferably at least four of the nucleotides are phosphorothiote substitutions; more specifically, 4-11 of the nucleotides are phosphorothiote substitutions); phosphorodithioate, 5'-thiophosphate, or methylphosphonate backbone chemistry or a combination thereof. In addition to one or more backbone chemistries described above, the RNase H activating region can also comprise a variety of sugar chemistries. For example, the RNase H activating region can comprise deoxyribose, arabino, fluoroarabino or a combination thereof, nucleotide sugar chemistry. Those skilled in the art will recognize that the foregoing are non-limiting examples and that any combination of phosphate, sugar and base chemistry of a nucleic acid that supports the activity of RNase H enzyme is within the scope of the definition of the RNase H activating region and the instant invention.

The term "2-5A antisense chimera" as used herein, refers to an antisense oligonucleotide containing a 5'-phosphorylated 2'-5'-linked adenylate residue. These chimeras bind to target RNA in a sequence-specific manner and activate a cellular 2-5A-dependent ribonuclease which, in turn, cleaves the target RNA (Torrence et al., 1993 Proc. Natl. Acad. Sci. USA 90, 1300; Silverman et al., 2000, Methods Enzymol., 313, 522-533; Player and Torrence, 1998, Pharmacol. Ther., 78, 55-113).

The term "triplex forming oligonucleotides" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth et. al., 2000, Biochim. Biophys. Acta, 1489, 181-206).

The term "gene" it as used herein, refers to a nucleic acid that encodes an RNA, for example, nucleic acid sequences including but not limited to structural genes encoding a polypeptide.

The term "pathogenic protein" as used herein, refers to endogenous or exongenous proteins that are associated with a disease state or condition, for example a particular cancer or viral infection.

The term "complementarity" refers to the ability of a nucleic acid to form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well known in the art (see, e.g., Turner et al., 1987, CSH Symp. Quant. Biol. LH pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

The term "RNA" as used herein, refers to a molecule comprising at least one ribonucleotide residue. By "ribonucleotide" or "2'-OH" is meant a nucleotide with a hydroxyl group at the 2' position of a β-D-ribo-furanose moiety.

The term "decoy RNA" as used herein, refers to a RNA molecule or aptamer that is designed to preferentially bind to a predetermined ligand. Such binding can result in the inhibition or activation of a target molecule. The decoy RNA or aptamer can compete with a naturally occurring binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990, Cell, 63, 601-608). This is but a specific example and those in the art will recognize that other embodiments can be readily generated using techniques generally known in the art, see for example Gold et al., 1995, Annu. Rev. Biochem., 64, 763; Brody and Gold, 2000, J. Biotechnol., 74, 5; Sun, 2000, Curr. Opin. Mol. Ther., 2, 100; Kusser, 2000, J. Biotechnol., 74, 27; Hermann and Patel, 2000, Science, 287, 820; and Jayasena, 1999, Clinical Chemistry, 45, 1628. Similarly, a decoy RNA can be designed to bind to a receptor and block the binding of an effector molecule or a decoy RNA can be designed to bind to receptor of interest and prevent interaction with the receptor.

The term "cell" as used herein, refers to its usual biological sense, and does not refer to an entire multicellular organism. The cell can, for example, be in vitro, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The term "highly conserved sequence region" as used herein, refers to a nucleotide sequence of one or more regions in a target gene does not vary significantly from one generation to the other or from one biological system to the other.

The term "non-nucleotide" as used herein, refers to any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine.

The term "nucleotide" as used herein, refers to a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N-6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleoside bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "nucleoside" as used herein, refers to a heterocyclic nitrogenous base in N-glycosidic linkage with a sugar. Nucleosides are recognized in the art to include natural bases (standard), and modified bases well known in the art. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, modified nucleosides, non-natural nucleosides, non-standard nucleosides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleoside bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "cap structure" as used herein, refers to chemical modifications, which have been incorporated at either terminus of the oligonucleotide (see for example Wincott et al., WO 97/26270, incorporated by reference herein). These terminal modifications protect the nucleic acid molecule from exonuclease degradation, and can help in delivery and/or localization within a cell. The cap can be present at the 5'-terminus (5'-cap) or at the 3'-terminus (3'-cap) or can be present on both terminus. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

The term "abasic" as used herein, refers to sugar moieties lacking a base or having other chemical groups in place of a base at the 1' position, for example a 3',3'-linked or 5',5'-linked deoxyabasic ribose derivative (for more details see Wincott et al., International PCT publication No. WO 97/26270).

The term "unmodified nucleoside" as used herein, refers to one of the bases adenine, cytosine, guanine, thymine, uracil joined to the 1' carbon off-β-D-ribo-furanose.

The term "modified nucleoside" as used herein, refers to any nucleotide base which contains a modification in the chemical structure of an unmodified nucleotide base, sugar and/or phosphate.

The term "consists essentially of" as used herein, is meant that the active nucleic acid molecule of the invention, for example, an enzymatic nucleic acid molecule, contains an enzymatic center or core equivalent to those in the examples, and binding arms able to bind RNA such that cleavage at the target site occurs. Other sequences can be present which do not interfere with such cleavage. Thus, a core region can, for example, include one or more loop, stem-loop structure, or linker which does not prevent enzymatic activity. For example, a core sequence for a hammerhead enzymatic nucleic acid can comprise a conserved sequence, such as 5'-CUGAUGAG-3' and 5'-CGAA-3' connected by "X", where X is 5'-GCCGUUAGGC-3' (SEQ ID NO 1), or any other Stem II region known in the art, or a nucleotide and/or non-nucleotide linker. Similarly, for other nucleic acid molecules of the instant invention, such as Inozyme, G-cleaver, amberzyme, zinzyme, DNAzyme, antisense, 2-5A antisense, triplex forming nucleic acid, and decoy nucleic acids, other sequences or non-nucleotide linkers can be present that do not interfere with the function of the nucleic acid molecule.

Sequence X can be a linker of ≧2 nucleotides in length, preferably 3, 4, 5, 6, 7, 8, 9, 10, 15, 20, 26, 30, where the nucleotides can preferably be internally base-paired to form a stem of preferably 2 base pairs. In yet another embodiment, the nucleotide linker X can be a nucleic acid aptamer, such as an ATP aptamer, HIV Rev aptamer (RRE), HIV Tat aptamer (TAR) and others (for a review see Gold et al., 1995, Arum. Rev. Biochem., 64, 763; and Szostak & Ellington, 1993, in The RNA World, ed. Gesteland and Atkins, pp. 511, CSH Laboratory Press). A "nucleic acid aptamer" as used herein is meant to indicate a nucleic acid sequence capable of interacting with a ligand. The ligand can be any natural or a synthetic molecule, including but not limited to a resin, metabolites, nucleosides, nucleotides, drugs, toxins, transition state analogs, peptides, lipids, proteins, amino acids, nucleic acid molecules, hormones, carbohydrates, receptors, cells, viruses, bacteria and others.

Alternatively or in addition, sequence X can be a non-nucleotide linker. Non-nucleotides can include abasic nucleotide, polyether, polyamine, polyamide, peptide, carbohydrate, lipid, or polyhydrocarbon compounds. Specific examples include those described by Seela and Kaiser, Nucleic Acids Res. 1990, 18:6353 and Nucleic Acids Res. 1987, 15:3113; Cload and Schepartz, J. Am. Chem. Soc. 1991, 113:6324; Richardson and Schepartz, J. Am. Chem. Soc. 1991, 113:5109; Ma et al., Nucleic Acids Res. 1993, 21:2585 and Biochemistry 1993, 32:1751; Durand et al., Nucleic Acids Res. 1990, 18:6353; McCurdy et al., Nucleosides & Nucleotides 1991, 10:287; Jschke et al., Tetrahedron Lett. 1993, 34:301; Ono et al., Biochemistry 1991, 30:9914; Arnold et al., International Publication No. WO 89/02439; Usman et al., International Publication No. WO 95/06731; Dudycz et al., International Publication No. WO 95/11910 and Ferentz and Verdine, J. Am. Chem. Soc. 1991, 113:4000, all hereby incorporated by reference herein. A "non-nucleotide" further means any group or compound which can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine. Thus, in a preferred embodiment, the invention features an enzymatic nucleic acid molecule having one or more non-nucleotide moieties, and having enzymatic activity to cleave an RNA or DNA molecule.

The term "patient" as used herein, refers to an organism, which is a donor or recipient of explanted cells or the cells themselves. "Patient" also refers to an organism to which the nucleic acid molecules of the invention can be administered. Preferably, a patient is a mammal or mammalian cells. More preferably, a patient is a human or human cells.

The term "enhanced enzymatic activity" as used herein, includes activity measured in cells and/or in vivo where the activity is a reflection of both the catalytic activity and the stability of the nucleic acid molecules of the invention. In this invention, the product of these properties can be increased in vivo compared to an all RNA enzymatic nucleic acid or all DNA enzyme. In some cases, the activity or stability of the nucleic acid molecule can be decreased (i.e., less than tenfold), but the overall activity of the nucleic acid molecule is enhanced, in vivo.

By "comprising" is meant including, but not limited to, whatever follows the word "comprising". Thus, use of the term "comprising" indicates that the listed elements are required or mandatory, but that other elements are optional and can or can not be present. By "consisting of" is meant including, and limited to, whatever follows the phrase "consisting of". Thus, the phrase "consisting of" indicates that the listed elements are required or mandatory, and that no other elements can be present.

The term "negatively charged molecules" as used herein, refers to molecules such as nucleic acid molecules (e.g., RNA, DNA, oligonucleotides, mixed polymers, peptide nucleic acid, and the like), peptides (e.g., polyaminoacids, polypeptides, proteins and the like), nucleotides, pharmaceutical and biological compositions, that have negatively charged groups that can ion-pair with the positively charged head group of the cationic lipids of the invention.

The term "coupling" as used herein, refers to a reaction, either chemical or enzymatic, in which one atom, moiety, group, compound or molecule is joined to another atom, moiety, group, compound or molecule.

The terms "deprotection" or "deprotecting" as used herein, refers to the removal of a protecting group.

The term "alkyl" as used herein refers to a saturated aliphatic hydrocarbon, including straight-chain, branched-chain "isoalkyl", and cyclic alkyl groups. The term "alkyl" also comprises alkoxy, alkyl-thio, alkyl-thio-alkyl, alkoxyalkyl, alkylamino, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. Preferably, the alkyl group has 1 to 12 carbons. More preferably it is a lower alkyl of from about 1 to about 7 carbons, more preferably about 1 to about 4 carbons. The alkyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. The term "alkyl" also includes alkenyl groups containing at least one carbon-carbon double bond, including straight-chain, branched-chain, and cyclic groups. Preferably, the alkenyl group has about 2 to about 12 carbons. More preferably it is a lower alkenyl of from about 2 to about 7 carbons, more preferably about 2 to about 4 carbons. The alkenyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. The term "alkyl" also includes alkynyl groups containing at least one carbon-carbon triple bond, including straight-chain, branched-chain, and cyclic groups. Preferably, the alkynyl group has about 2 to about 12 carbons. More preferably it is a lower alkynyl of from about 2 to about 7 carbons, more preferably about 2 to about 4 carbons. The alkynyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. Alkyl groups or moieties of the invention can also include aryl, alkylaryl, carbocyclic aryl, heterocyclic aryl, amide and ester groups. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from about 1 to about 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

The term "alkoxyalkyl" as used herein refers to an alkyl-O-alkyl ether, for example, methoxyethyl or ethoxymethyl.

The term "alkyl-thio-alkyl" as used herein refers to an alkyl-O-alkyl thioether, for example, methylthiomethyl or methylthioethyl.

The term "amino" as used herein refers to a nitrogen containing group as is known in the art derived from ammonia by the replacement of one or more hydrogen radicals by organic radicals. For example, the terms "aminoacyl" and "aminoalkyl" refer to specific N-substituted organic radicals with acyl and alkyl substituent groups respectively.

The term "amination" as used herein refers to a process in which an amino group or substituted amine is introduced into an organic molecule.

The term "exocyclic amine protecting moiety" as used herein refers to a nucleobase amino protecting group compatible with oligonucleotide synthesis, for example, an acyl or amide group.

The term "alkenyl" as used herein refers to a straight or branched hydrocarbon of a designed number of carbon atoms containing at least one carbon-carbon double bond. Examples of "alkenyl" include vinyl, allyl, and 2-methyl-3-heptene.

The term "alkoxy" as used herein refers to an alkyl group of indicated number of carbon atoms attached to the parent molecular moiety through an oxygen bridge. Examples of alkoxy groups include, for example, methoxy, ethoxy, propoxy and isopropoxy.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

The term "aryl" as used herein refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkenyl" as used herein refers to a C3-C8 cyclic hydrocarbon containing at least one carbon-carbon double bond. Examples of cycloalkenyl include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "cycloalkyl" as used herein refers to a C3-C8 cyclic hydrocarbon. Examples of cycloalkyl include cyclopropyl, cyclobutyl, cyclopentyl, cyclohexyl, cycloheptyl and cyclooctyl.

The term "cycloalkylalkyl," as used herein, refers to a C3-C7 cycloalkyl group attached to the parent molecular moiety through an alkyl group, as defined above. Examples of cycloalkylalkyl groups include cyclopropylmethyl and cyclopentylethyl.

The terms "halogen" or "halo" as used herein refers to indicate fluorine, chlorine, bromine, and iodine.

The term "heterocycloalkyl," as used herein, refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrrolidinyl.

The term "heteroaryl" as used herein refers to an aromatic ring system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "C1-C6 hydrocarbyl" as used herein refers to straight, branched, or cyclic alkyl groups having 1-6 carbon atoms, optionally containing one or more carbon-carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentene, cyclopropylmethyl, cyclopropyl, cyclohexylmethyl, cyclohexyl and propargyl. When reference is made herein to C1-C6 hydrocarbyl containing one or two double or triple bonds it is understood that at least two carbons are present in the alkyl for one double or triple bond, and at least four carbons for two double or triple bonds.

The term "protecting group" as used herein, refers to groups known in the art that are readily introduced and removed from an atom, for example O, N, P, or S. Protecting groups are used to prevent undesirable reactions from taking place that can compete with the formation of a specific compound or intermediate of interest. See also "Protective Groups in Organic Synthesis", 3rd Ed., 1999, Greene, T. W. and related publications.

The term "nitrogen protecting group," as used herein, refers to groups known in the art that are readily introduced on to and removed from a nitrogen. Examples of nitrogen protecting groups include Boc, Cbz, benzoyl, and benzyl. See also "Protective Groups in Organic Synthesis", 3rd Ed., 1999, Greene, T. W. and related publications.

The term "hydroxy protecting group," or "hydroxy protection" as used herein, refers to groups known in the art that are readily introduced on to and removed from an oxygen, specifically an —OH group. Examples of hyroxy protecting groups include trityl or substituted trityl goups, such as monomethoxytrityl and dimethoxytrityl, or substituted silyl groups, such as tert-butyldimethyl, trimethylsilyl, or tert-butyldiphenyl silyl groups. See also "Protective Groups in Organic Synthesis", 3rd Ed., 1999, Greene, T. W. and related publications.

The term "acyl" as used herein refers to —C(O)R groups, wherein R is an alkyl or aryl.

The term "phosphorus containing group" as used herein, refers to a chemical group containing a phosphorus atom. The phosphorus atom can be trivalent or pentavalent, and can be substituted with O, H, N, S, C or halogen atoms. Examples of phosphorus containing groups of the instant invention include but are not limited to phosphorus atoms substituted with O, H, N, S, C or halogen atoms, comprising phosphonate, alkylphosphonate, phosphate, diphosphate, triphosphate, pyrophosphate, phosphorothioate, phosphorodithioate, phosphoramidate, phosphoramidite groups, nucleotides and nucleic acid molecules.

The term "phosphine" or "phosphite" as used herein refers to a trivalent phosphorus species, for example compounds having Formula XXXII:

wherein R can include the groups:

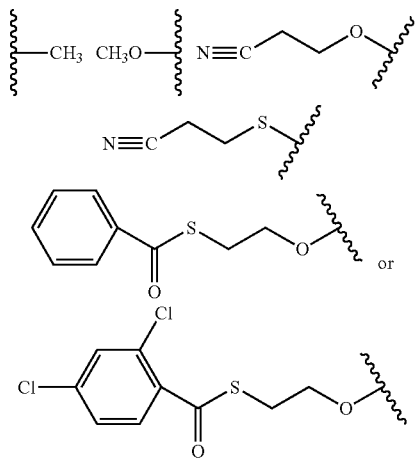

and wherein S and T independently include the groups:

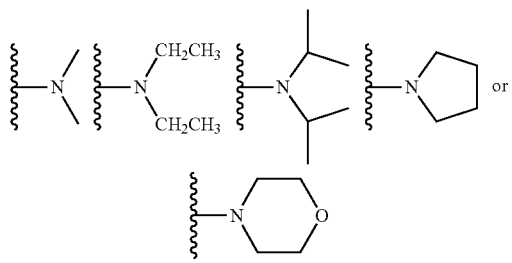

The term "phosphate" as used herein refers to a pentavalent phosphorus species, for example a compound having Formula XXXIV:

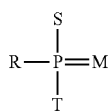

wherein R includes the groups:

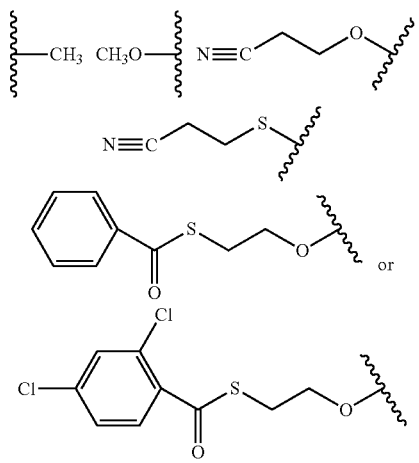

and wherein S and T each independently can be a sulfur or oxygen atom or a group which can include:

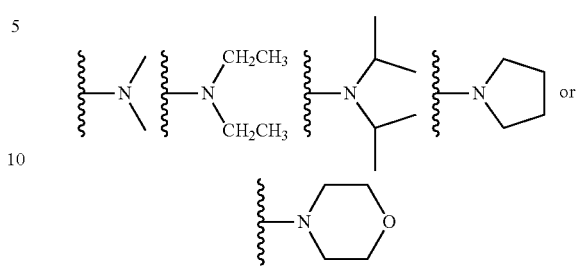

and wherein M comprises a sulfur or oxygen atom. The phosphate of the invention can comprise a nucleotide phosphate, wherein any R, S, or T in Formula XXXIV comprises a linkage to a nucleic acid or nucleoside.

The term "cationic salt" as used herein refers to any organic or inorganic salt having a net positive charge, for example a triethylammonium (TEA) salt.

The term "degradable linker" as used herein, refers to linker moieties that are capable of cleavage under various conditions. Conditions suitable for cleavage can include but are not limited to pH, UV irradiation, enzymatic activity, temperature, hydrolysis, elimination, and substitution reactions, and thermodynamic properties of the linkage.

The term "photolabile linker" as used herein, refers to linker moieties as are known in the art, that are selectively cleaved under particular UV wavelengths. Compounds of the invention containing photolabile linkers can be used to deliver compounds to a target cell or tissue of interest, and can be subsequently released in the presence of a UV source.

The term "nucleic acid conjugates" as used herein, refers to nucleoside, nucleotide and oligonucleotide conjugates.

The term "folate" as used herein, refers to analogs and derivatives of folic acid, for example antifolates, dihydrofoloates, tetrahydrofolates, tetrahydrorpterins, folinic acid, pteropolyglutamic acid, 1-deza, 3-deaza, 5-deaza, 8-deaza, 10-deaza, 1,5-deaza, 5,10 dideaza, 8,10-dideaza, and 5,8-dideaza folates, antifolates, and pteroic acid derivatives.

The term "compounds with neutral charge" as used herein, refers to compositions which are neutral or uncharged at neutral or physiological pH. Examples of such compounds are cholesterol and other steroids, cholesteryl hemisuccinate (CHEMS), dioleoyl phosphatidyl choline, distearoylphosphotidyl choline (DSPC), fatty acids such as oleic acid, phosphatidic acid and its derivatives, phosphatidyl serine, polyethylene glycol-conjugated phosphatidylamine, phosphatidylcholine, phosphatidylethanolamine and related variants, prenylated compounds including farnesol, polyprenols, tocopherol, and their modified forms, diacylsuccinyl glycerols, fusogenic or pore forming peptides, dioleoylphosphotidylethanolamine (DOPE), ceramide and the like.

The term "lipid aggregate" as used herein refers to a lipid-containing composition wherein the lipid is in the form of a liposome, micelle (non-lamellar phase) or other aggregates with one or more lipids.

The term "biological system" as used herein, refers to a eukaryotic system or a prokaryotic system, can be a bacterial cell, plant cell or a mammalian cell, or can be of plant origin, mammalian origin, yeast origin, Drosophila origin, or archebacterial origin.

The term "systemic administration" as used herein refers to the in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as the cancer cells.

The term "pharmacological composition" or "pharmaceutical formulation" refers to a composition or formulation in a form suitable for administration, for example, systemic administration, into a cell or patient, preferably a human. Suitable forms, in part, depend upon the use or the route of entry, for example oral, transdermal, or by injection. Such forms should not prevent the composition or formulation to reach a target cell (i.e., a cell to which the negatively charged polymer is targeted).

Other features and advantages of the invention will be apparent from the following description of the preferred embodiments thereof, and from the claims.

DESCRIPTION OF THE PREFERRED EMBODIMENTS

The drawings will be first described briefly.

DRAWINGS

FIG. 1 shows examples of chemically stabilized ribozyme motifs. HH Rz, represents hammerhead ribozyme motif (Usman et al., 1996, Curr. Op. Struct. Bio., 1, 527); NCH Rz represents the NCH ribozyme motif (Ludwig & Sproat, International PCT Publication No. WO 98/58058); G-Cleaver, represents G-cleaver ribozyme motif (Kore et al., 1998, Nucleic Acids Research 26, 4116-4120, Eckstein et al., International PCT publication No. WO 99/16871). N or n, represent independently a nucleotide which can be same or different and have complementarity to each other; rI, represents ribo-Inosine nucleotide; arrow indicates the site of cleavage within the target. Position 4 of the HH Rz and the NCH Rz is shown as having 2'-C-allyl modification, but those skilled in the art will recognize that this position can be modified with other modifications well known in the art, so long as such modifications do not significantly inhibit the activity of the ribozyme.

FIG. 12 shows an alternative synthetic scheme for post-synthetic modification of a nucleic acid molecule to produce a folate conjugate.

METHOD OF USE

Figure 1:
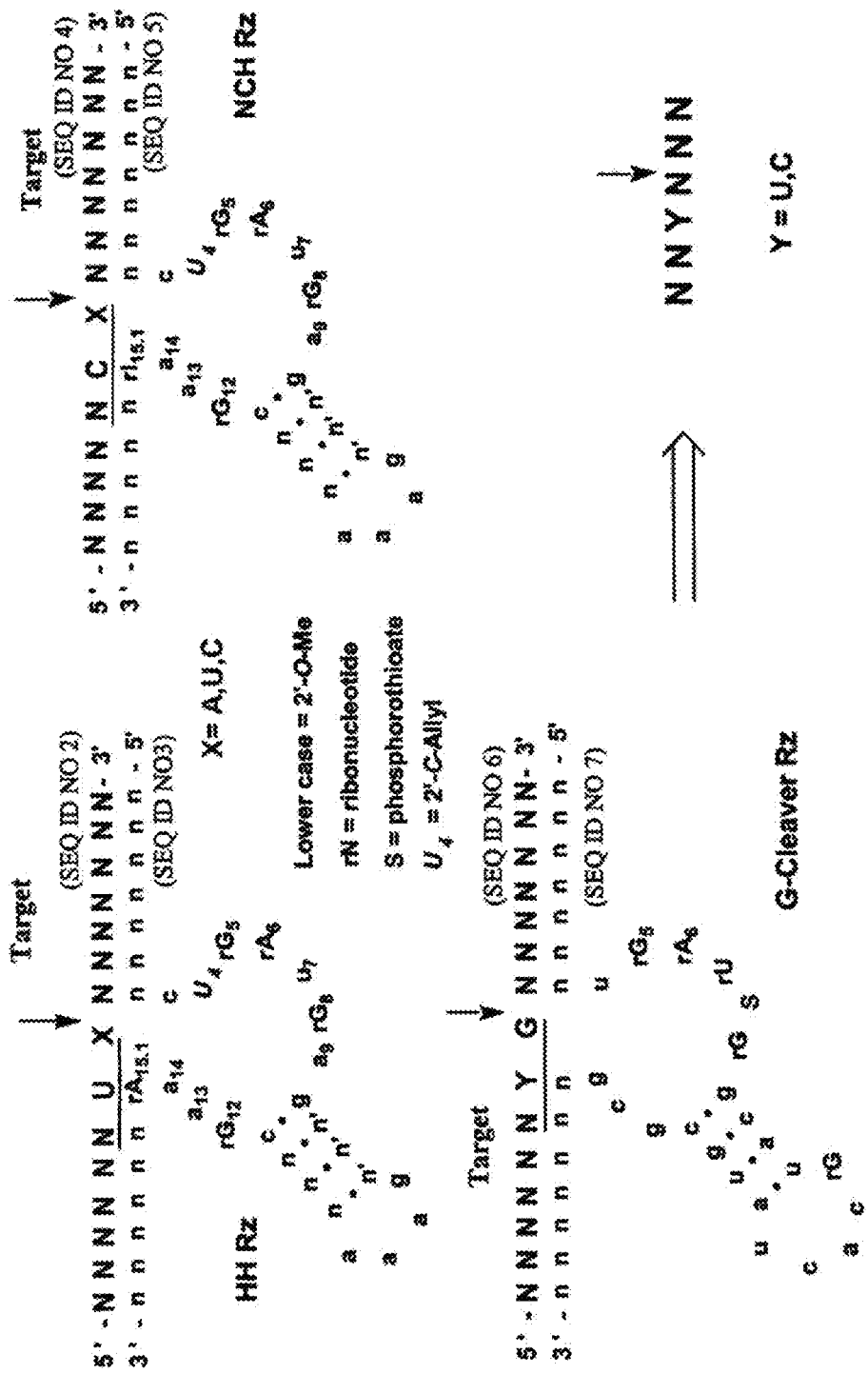
Figure 2:
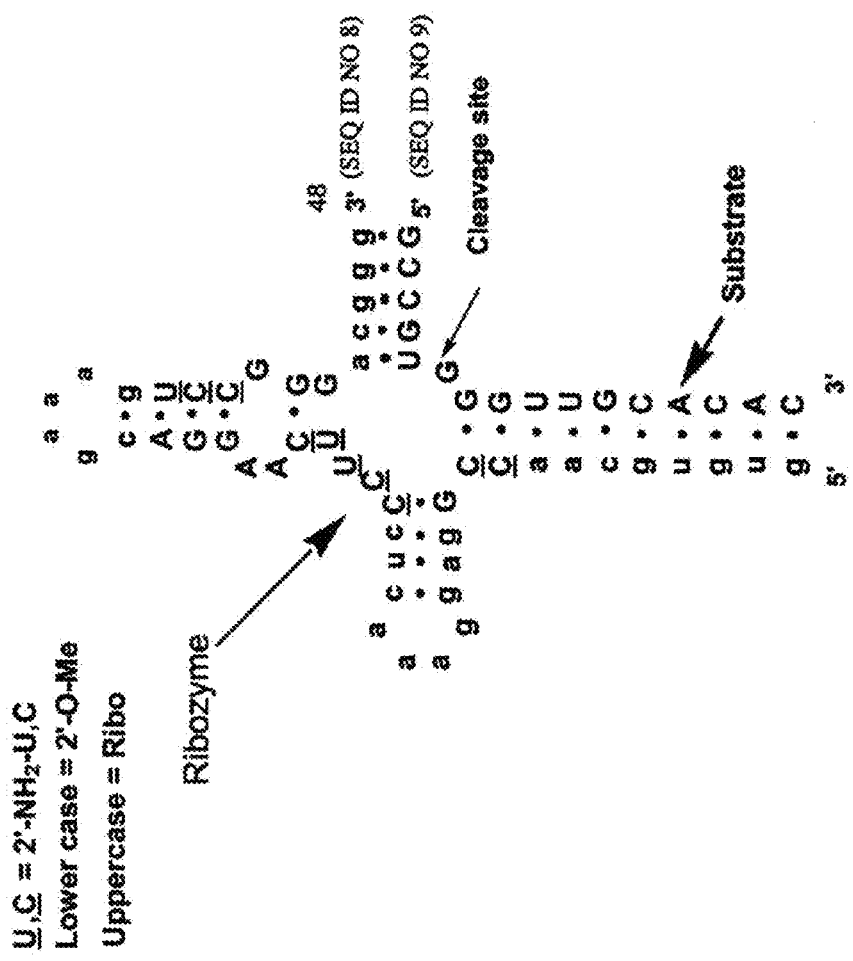
FIG. 2 shows an example of the Amberzyme ribozyme motif that is chemically stabilized (see for example Beigelman et al., International PCT publication No. WO 99/55857).
Figure 3:
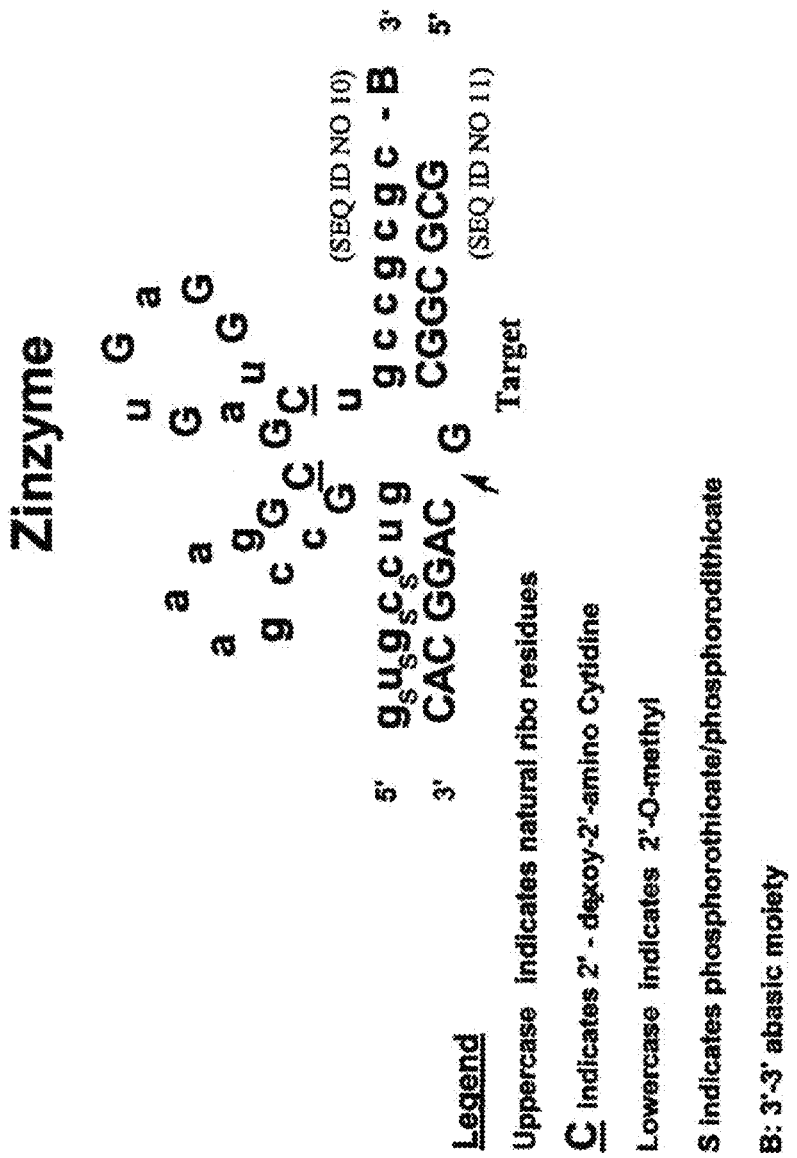
FIG. 3 shows an example of the Zinzyme A ribozyme motif that is chemically stabilized (see for example Beigelman et al., Beigelman et al., International PCT publication No. WO 99/55857).
Figure 4:
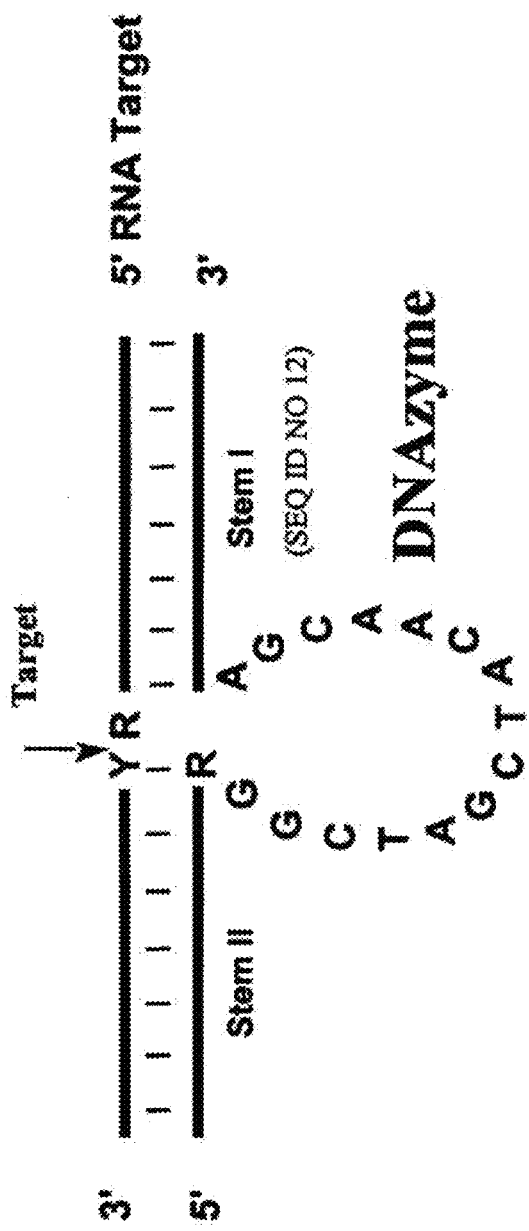
FIG. 4 shows an example of a DNAzyme motif described by Santoro et al., 1997, PNAS, 94, 4262.

The compositions and conjugates of the instant invention can be used to administer pharmaceutical agents. Pharmaceutical agents prevent, inhibit the occurrence, or treat (alleviate a symptom to some extent, preferably all of the symptoms) of a disease state in a patient.

Generally, the compounds of the instant invention are introduced by any standard means, with or without stabilizers, buffers, and the like, to form a pharmaceutical composition. For use of a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the like.

The present invention also includes pharmaceutically acceptable formulations of the compounds described above, preferably in combination with the molecule(s) to be delivered. These formulations include salts of the above compounds, e.g., acid addition salts, for example, salts of hydrochloric, hydrobromic, acetic acid, and benzene sulfonic acid.

In one embodiment, the invention features the use of the compounds of the invention in a composition comprising surface-modified liposomes containing poly (ethylene glycol) lipids (PEG-modified, or long-circulating liposomes or stealth liposomes). In another embodiment, the invention features the use of compounds of the invention covalently attached to polyethylene glycol. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwataet al., Chem. Pharm. Bull. 1995, 43, 1005-1011). Such compositions have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating compositions enhance the pharmacokinetics and pharmacodynamics of therapeutic compounds, such as DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating compositions are also likely to protect drugs from nuclease degradation to a greater extent compared to cationic liposomes, based on their ability to avoid accumulation in metabolically aggressive MPS tissues such as the liver and spleen.

The present invention also includes a composition(s) prepared for storage or administration that includes a pharmaceutically effective amount of the desired compound(s) in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A.R. Gennaro edit. 1985) hereby incorporated by reference herein. For example, preservatives, stabilizers, dyes and flavoring agents can be included in the composition. Examples of such agents include but are not limited to sodium benzoate, sorbic acid and esters of p-hydroxybenzoic acid. In addition, antioxidants and suspending agents can be included in the composition.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer. Furthermore, the compounds of the invention and formulations thereof can be administered to a fetus via administration to the mother of a fetus.

The compounds of the invention and formulations thereof can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example, sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The compounds of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The compounds of the present invention can also be administered to a patient in combination with other therapeutic compounds to increase the overall therapeutic effect. The use of multiple compounds to treat an indication can increase the beneficial effects while reducing the presence of side effects.

Synthesis of Nucleic Acid Molecules

Synthesis of nucleic acids greater than 100 nucleotides in length is difficult using automated methods, and the therapeutic cost of such molecules is prohibitive. In this invention, small nucleic acid motifs ("small refers to nucleic acid motifs less than about 100 nucleotides in length, preferably less than about 80 nucleotides in length, and more preferably less than about 50 nucleotides in length; e.g., antisense oligonucleotides, hammerhead or the NCH ribozymes) are preferably used for exogenous delivery. The simple structure of these molecules increases the ability of the nucleic acid to invade targeted regions of RNA structure. Exemplary molecules of the instant invention are chemically synthesized, and others can similarly be synthesized.

Oligonucleotides (eg; antisense GeneBlocs) are synthesized using protocols known in the art as described in Caruthers et al., 1992, *Methods in Enzymology* 211, 3-19, Thompson et al., International PCT Publication No. WO 99/54459, Wincott et al., 1995, *Nucleic Acids Res.* 23, 2677-2684, Wincott et al., 1997, *Methods Mol. Bio.*, 74, 59, Brennan et al., 1998, *Biotechnol Bioeng.*, 61, 33-45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 2.5 min coupling step for 2-O-methylated nucleotides and a 45 sec coupling step for 2'-deoxy nucleotides. Table II outlines the amounts and the contact times of the reagents used in the synthesis cycle. Alternatively, syntheses at the 0.2 µmol scale can be performed on a 96-well plate synthesizer, such as the instrument produced by Protogene (Palo Alto, Calif.) with minimal modification to the cycle. In a non-limiting example, a 33-fold excess (60 µL of 0.11 M=6.6 µmol) of 2'-O-methyl phosphoramidite and a 105-fold excess of S-ethyl tetrazole (60 µL of 0.25 M=15 µmol) can be used in each coupling cycle of 2'-O-methyl residues relative to polymer-bound 5'-hydroxyl. In a non-limiting example, a 22-fold excess (40 µL of 0.11 M=4.4 µmol) of deoxy phosphoramidite and a 70-fold excess of S-ethyl tetrazole (40 µL of 0.25 M=10 µmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include but are not limited to; detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PERSEPTIVET™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the antisense oligonucleotides is performed as follows: the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. Standard drying or lyophilization methods known to those skilled in the art can be used.

The method of synthesis used for normal RNA including certain enzymatic nucleic acid molecules follows the procedure as described in Usman et al., 1987, *J. Am. Chem. Soc.*, 109, 7845; Scaringe et al., 1990, *Nucleic Acids Res.*, 18, 5433; and Wincott et al., 1995, *Nucleic Acids Res.* 23, 2677-2684 Wincott et al., 1997, *Methods Mol. Bio.*, 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 7.5 min coupling step for alkylsilyl protected nucleotides and a 2.5 min coupling step for 2'-O -methylated nucleotides. Table II outlines the amounts and the contact times of the reagents used in the synthesis cycle. Alternatively, syntheses at the 0.2 µmol scale can be done on a 96-well plate synthesizer, such as the instrument produced by Protogene (Palo Alto, Calif.) with minimal modification to the cycle. A 33-fold excess (60 µL, of 0.11 M=6.6 µmol of 2'-O-methyl phosphoramidite and a 75-fold excess of S-ethyl tetrazole (60 µL of 0.25 M=15 µmol) can be used in each coupling cycle of 2'-O-methyl residues relative to polymer-bound 5'-hydroxyl. A 66-fold excess (120 µL of 0.11 M=13.2 µmol) of alkylsilyl (ribo) protected phosphoramidite and a 150-fold excess of S-ethyl tetrazole (120 µL of 0.25 M=30 µmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include; detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH: MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 µL of a solution of 1.5 mL N-methylpyrrolidinone, 750 µL TEA and 1 mL TEA~3HF to provide a 1.4 M HF concentration) and heated to 65° C. After 1.5 h, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine/DMSO:1/1 (0.8 mL) at 65° C. for 15 min. The vial is brought to r.t. TEA~3HF (0.1 mL) is added and the vial is heated at 65° C. for 15 min. The sample is cooled at ~20° C. and then quenched with 1.5 M $NH_4HCO_3$.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% TFA for 13 min. The cartridge is then washed again with water, salt exchanged with 1 M NaCl and washed with water again. The oligonucleotide is then eluted with 30% acetonitrile.

Inactive hammerhead ribozymes or binding attenuated control ((BAC) oligonucleotides) are synthesized by substituting a U for $G_5$ and a U for $A_{14}$ (numbering from Hertel, K. J., et al., 1992, *Nucleic Acids Res.*, 20, 3252). Similarly, one or more nucleotide substitutions can be introduced in other enzymatic nucleic acid molecules to inactivate the molecule and such molecules can serve as a negative control.

The average stepwise coupling yields are typically >98% (Wincott et al., 1995 *Nucleic Acids Res.* 23, 2677-2684). Those of ordinary skill in the art will recognize that the scale of synthesis can be adapted to be larger or smaller than the example described above including, but not limited to, 96 well format, with the ratio of chemicals used in the reaction being adjusted accordingly.

Alternatively, the nucleic acid molecules of the present invention can be synthesized separately and joined together post-synthetically, for example by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides*, 16, 951; Bellon et al., 1997, *Bioconjugate Chem.* 8, 204).

The nucleic acid molecules of the present invention are modified extensively to enhance stability by modification with nuclease resistant groups, for example, 2'-amino, 2'-C-allyl, 2'-flouro, 2'-O-methyl, 2'-H (for a review see Usman and Cedergren, 1992, *TIBS* 17, 34; Usman et al., 1994, *Nucleic Acids Symp. Ser.* 31, 163). Ribozymes are purified by gel electrophoresis using general methods or are purified by high pressure liquid chromatography (HPLC; See Wincott et al., Supra, the totality of which is hereby incorporated herein by reference) and are re-suspended in water.

Optimizing Activity of the Nucleic Acid Molecule of the Invention.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al., 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-H, nucleotide base modifications (for a review see Usman and Cedergren, 1992, *TIBS.* 17, 34; Usman et al., 1994, *Nucleic Acids Symp. Ser.* 31, 163; Burgin et al., 1996, *Biochemistry*, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. *Science,* 1991, 253, 314-317; Usman and Cedergren, *Trends in Biochem. Sci.*, 1992, 17, 334-339; Usman et al. International Publication PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39, 1131; Earnshaw and Gait, 1998, *Biopolymers (Nucleic acid Sciences)*, 48, 39-55; Verma and Eckstein, 1998, *Annu. Rev. Biochem.*, 67, 99-134; and Burlina et al., 1997, *Bioorg. Med. Chem.*, 5, 1999-2010; all of the references are hereby incorporated in their totality by reference herein). Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid molecules of the instant invention.

While chemical modification of oligonucleotide internucleotide linkages with phosphorothioate, phosphorothioate, and/or 5'-methylphosphonate linkages improves stability, too many of these modifications may cause some toxicity. Therefore, when designing nucleic acid molecules the amount of these internucleotide linkages should be minimized. Without being bound by any particular theory, the reduction in the concentration of these linkages should lower toxicity resulting in increased efficacy and higher specificity of these molecules.

Nucleic acid molecules having chemical modifications that maintain or enhance activity are provided. Such nucleic acid is also generally more resistant to nucleases than unmodified nucleic acid. Thus, in a cell and/or in vivo the activity can not be significantly lowered. Therapeutic nucleic acid molecules (e.g., enzymatic nucleic acid molecules and antisense nucleic acid molecules) delivered exogenously are optimally stable within cells until translation of the target RNA has been inhibited long enough to reduce the levels of the undesirable protein. This period of time varies between hours to days depending upon the disease state. The nucleic acid molecules should be resistant to nucleases in order to function as effective intracellular therapeutic agents. Improvements in the chemical synthesis of RNA and DNA (Wincott et al., 1995 *Nucleic Acids Res.* 23, 2677; Caruthers et al., 1992, *Methods in Enzymology* 211, 3-19 (incorporated by reference herein) have expanded the ability to modify nucleic acid molecules by introducing nucleotide modifications to enhance their nuclease stability as described above.

Use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules (including different motifs) and/or other chemical or biological molecules). The treatment of patients with nucleic acid molecules can also include combinations of different types of nucleic acid molecules.

In another embodiment, nucleic acid catalysts having chemical modifications that maintain or enhance enzymatic activity are provided. Such nucleic acids are also generally more resistant to nucleases than unmodified nucleic acid. Thus, in a cell and/or in vivo the activity of the nucleic acid can not be significantly lowered. As exemplified herein such enzymatic nucleic acids are useful in a cell and/or in vivo even if activity over all is reduced 10 fold (Burgin et al., 1996, *Biochemistry*, 35, 14090). Such enzymatic nucleic acids herein are said to "maintain" the enzymatic activity of an all RNA ribozyme or all DNA DNAzyme.

In another aspect the nucleic acid molecules comprise a 5' and/or a 3'-cap structure.

In another embodiment the 3'-cap includes, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

In one embodiment, the invention features modified enzymatic nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, *Nucleic Acid Analogues: Synthesis and Properties*, in *Modern Synthetic Methods*, VCH, 331-417, and Mesmaeker et al., 1994, *Novel Backbone Replacements for Oligonucleotides*, in *Carbohydrate Modifications in Antisense Research*, ACS, 24-39. These references are hereby incorporated by reference herein.

In connection with 2'-modified nucleotides as described for the invention, by "amino" is meant 2'—$NH_2$ or 2'-O—$NH_2$, which can be modified or unmodified. Such modified groups are described, for example, in Eckstein et al., U.S. Pat. No. 5,672,695 and Matulic-Adamic et al., WO 98/28317, respectively, which are both incorporated by reference in their entireties.

Various modifications to nucleic acid (e.g., antisense and ribozyme) structure can be made to enhance the utility of these molecules. For example, such modifications can enhance shelf-life, half-life in vitro, stability, and ease of introduction of such oligonucleotides to the target site, including e.g., enhancing penetration of cellular membranes and conferring the ability to recognize and bind to targeted cells.

Use of these molecules can lead to better treatment of disease progression by affording the possibility of combination therapies (e.g., multiple enzymatic nucleic acid molecules targeted to different genes, enzymatic nucleic acid molecules coupled with known small molecule inhibitors, or intermittent treatment with combinations of enzymatic nucleic acid molecules (including different enzymatic nucleic acid molecule motifs) and/or other chemical or biological molecules). The treatment of patients with nucleic acid molecules can also include combinations of different types of nucleic acid molecules. Therapies can be devised which include a mixture of enzymatic nucleic acid molecules (including different enzymatic nucleic acid molecule motifs), antisense and/or 2-5A chimera molecules to one or more targets to alleviate symptoms of a disease.

Indications

Particular disease states that can be treated using compounds and compositions of the invention include, but are not limited to, cancers and cancerous conditions such as breast, lung, prostate, colorectal, brain, esophageal, stomach, bladder, pancreatic, cervical, head and neck, and ovarian cancer, melanoma, lymphoma, glioma, multidrug resistant cancers, and/or viral infections including HIV, HBV, HCV, CMV, RSV, HSV, poliovirus, influenza, rhinovirus, west nile virus, Ebola virus, foot and mouth virus, and papilloma virus infection.

The molecules of the invention can be used in conjunction with other known methods, therapies, or drugs. For example, the use of monoclonal antibodies (eg; mAb IMC C225, mAB ABX-EGF) treatment, tyrosine kinase inhibitors (TKIs), for example OSI-774 and ZD1839, chemotherapy, and/or radiation therapy, are all non-limiting examples of a methods that can be combined with or used in conjunction with the compounds of the instant invention. Common chemotherapies that can be combined with nucleic acid molecules of the instant invention include various combinations of cytotoxic drugs to kill the cancer cells. These drugs include, but are not limited to, paclitaxel (Taxol), docetaxel, cisplatin, methotrexate, cyclophosphamide, doxorubin, fluorouracil carboplatin, edatrexate, gemcitabine, vinorelbine etc. Those skilled in the art will recognize that other drug compounds and therapies can be similarly be readily combined with the compounds of the instant invention are hence within the scope of the instant invention.

Diagnostic Uses

The compounds of this invention, for example, nucleic acid conjugate molecules, can be used as diagnostic tools to examine genetic drift and mutations within diseased cells or to detect the presence of a disease related RNA in a cell. The close relationship between, for example, enzymatic nucleic acid molecule activity and the structure of the target RNA allows the detection of mutations in any region of the molecule which alters the base-pairing and three-dimensional structure of the target RNA. By using multiple enzymatic nucleic acid molecules conjugates of the invention, one can map nucleotide changes which are important to RNA structure and function in vitro, as well as in cells and tissues. Cleavage of target RNAs with enzymatic nucleic acid molecules can be used to inhibit gene expression and define the role (essentially) of specified gene products in the progression of disease. In this manner, other genetic targets can be defined as important mediators of the disease. These experiments can lead to better treatment of the disease progression by affording the possibility of combinational therapies (e.g., multiple enzymatic nucleic acid molecules targeted to different genes, enzymatic nucleic acid molecules coupled with known small molecule inhibitors, or intermittent treatment with combinations of enzymatic nucleic acid molecules and/or other chemical or biological molecules). Other in vitro uses of enzymatic nucleic acid molecules of this invention are well known in the art, and include detection of the presence of mRNAs associated with a disease-related condition. Such RNA is detected by determining the presence of a cleavage product after treatment with an enzymatic nucleic acid molecule using standard methodology.

In a specific example, enzymatic nucleic acid molecules that are delivered to cells as conjugates and which cleave only wild-type or mutant forms of the target RNA are used for the assay. The first enzymatic nucleic acid molecule is used to identify wild-type RNA present in the sample and the second enzymatic nucleic acid molecule is used to identify mutant RNA in the sample. As reaction controls, synthetic substrates of both wild-type and mutant RNA are cleaved by both enzymatic nucleic acid molecules to demonstrate the relative enzymatic nucleic acid molecule efficiencies in the reactions and the absence of cleavage of the "non-targeted" RNA species. The cleavage products from the synthetic substrates also serve to generate size markers for the analysis of wild-type and mutant RNAs in the sample population. Thus each analysis requires two enzymatic nucleic acid molecules, two substrates and one unknown sample which is combined into six reactions. The presence of cleavage products is determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios are correlated with higher risk whether RNA levels are compared qualitatively or quantitatively. The use of enzymatic nucleic acid molecules in diagnostic applications contemplated by the instant invention is more fully described in George et al., U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842.

Additional Uses

Potential uses of sequence-specific enzymatic nucleic acid molecules of the instant invention that are delivered to cells as conjugates can have many of the same applications for the study of RNA that DNA restriction endonucleases have for the study of DNA (Nathans et al., 1975 Ann. Rev. Biochem. 44:273). For example, the pattern of restriction fragments can be used to establish sequence relationships between two related RNAs, and large RNAs can be specifically cleaved to fragments of a size more useful for study. The ability to engineer sequence specificity of the enzymatic nucleic acid molecule is ideal for cleavage of RNAs of unknown sequence. Applicant has described the use of nucleic acid molecules to down-regulate gene expression of target genes in bacterial, microbial, fungal, viral, and eukaryotic systems including plant, or mammalian cells.

EXAMPLE 1

Figure 5:
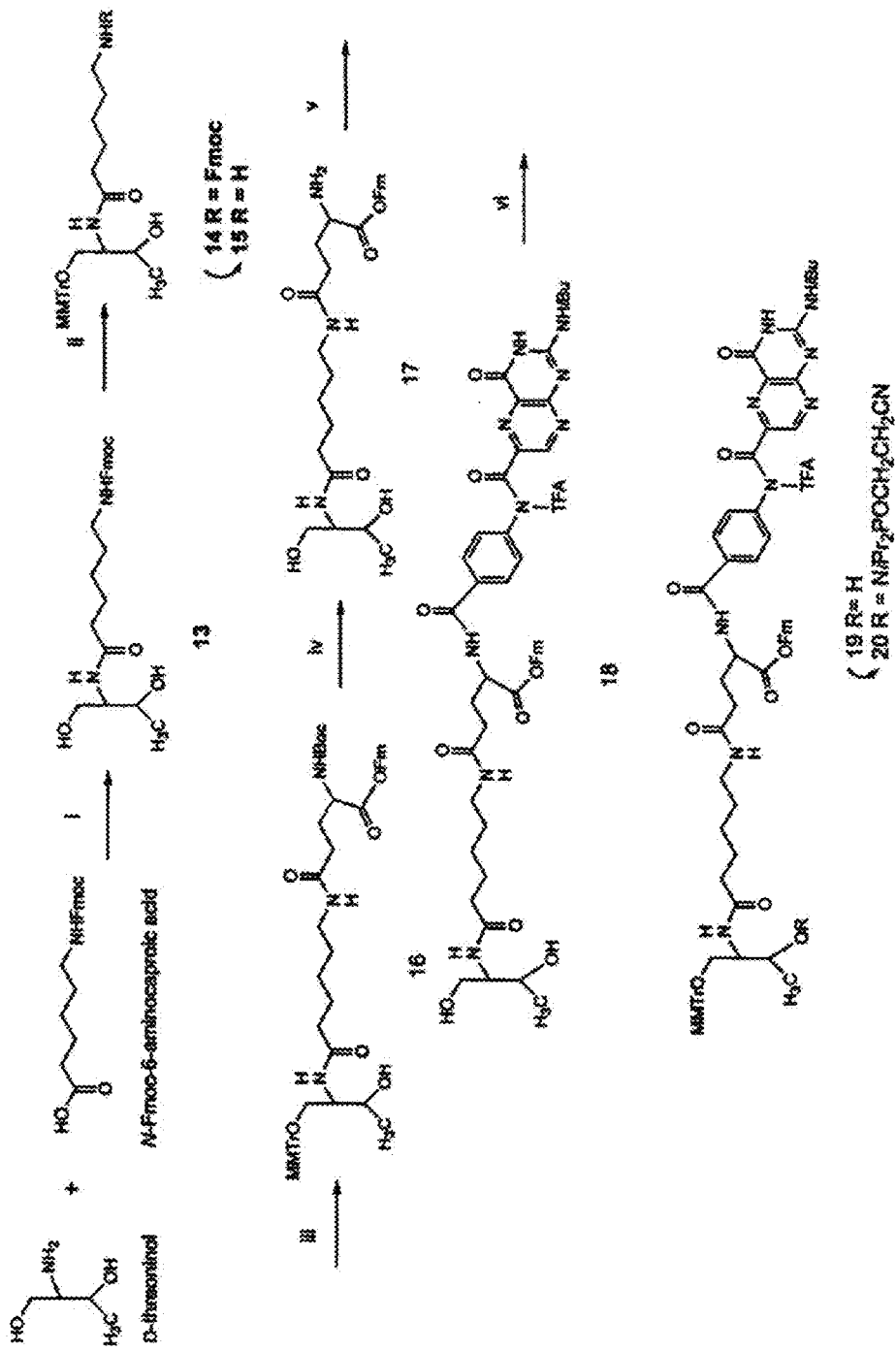
FIG. 5 shows a synthetic scheme for the synthesis of a folate conjugate of the instant invention.
Figure 6:
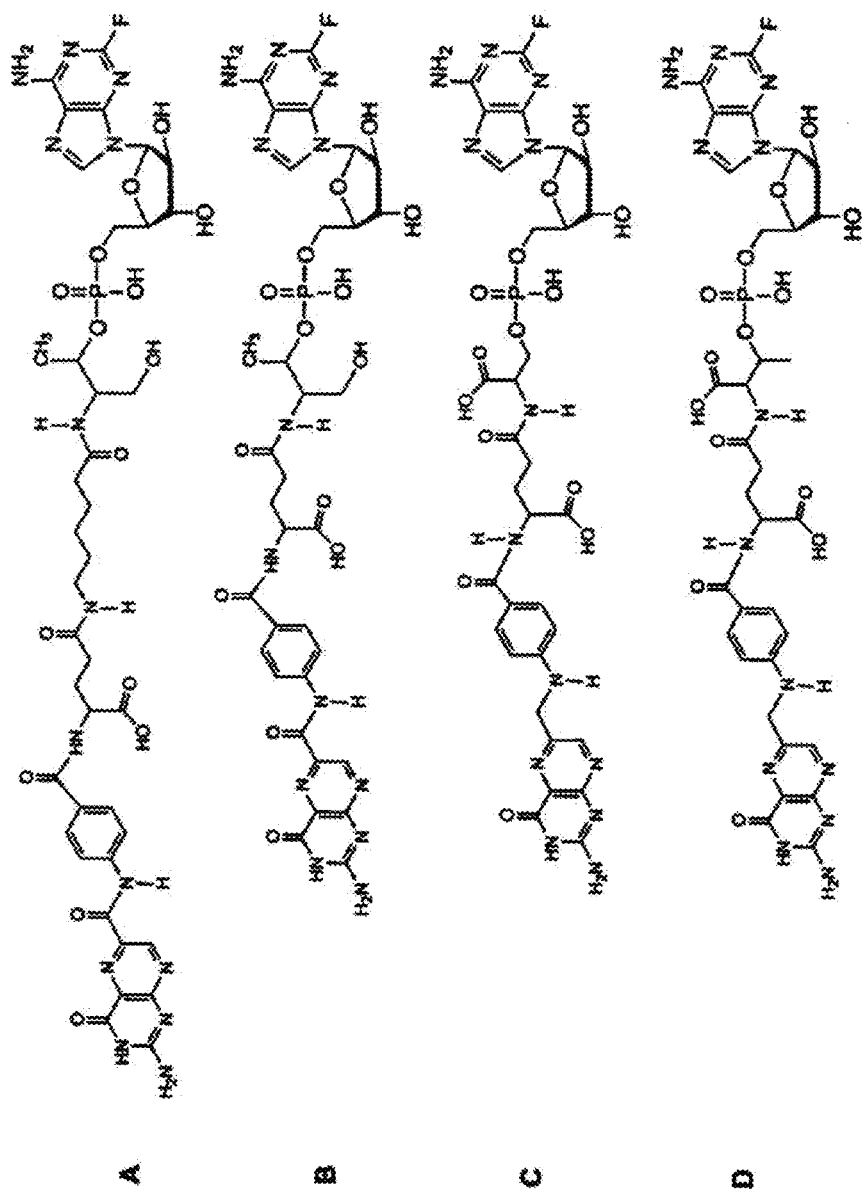
FIG. 6 shows representative examples of fludarabine-folate conjugate molecules of the invention.
Figure 7:
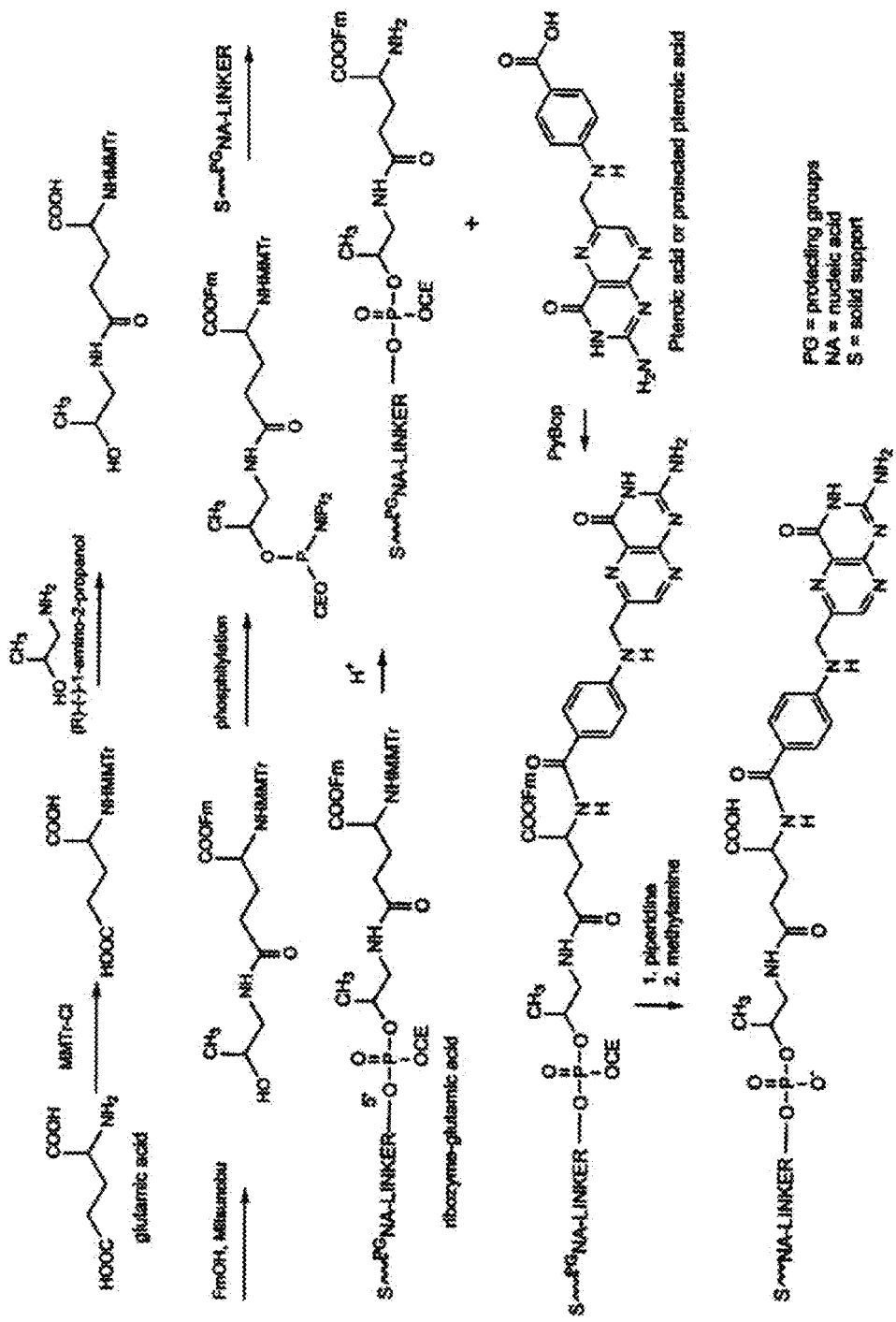
FIG. 7 shows a synthetic scheme for post-synthetic modification of a nucleic acid molecule to produce a folate conjugate.
Figure 8:
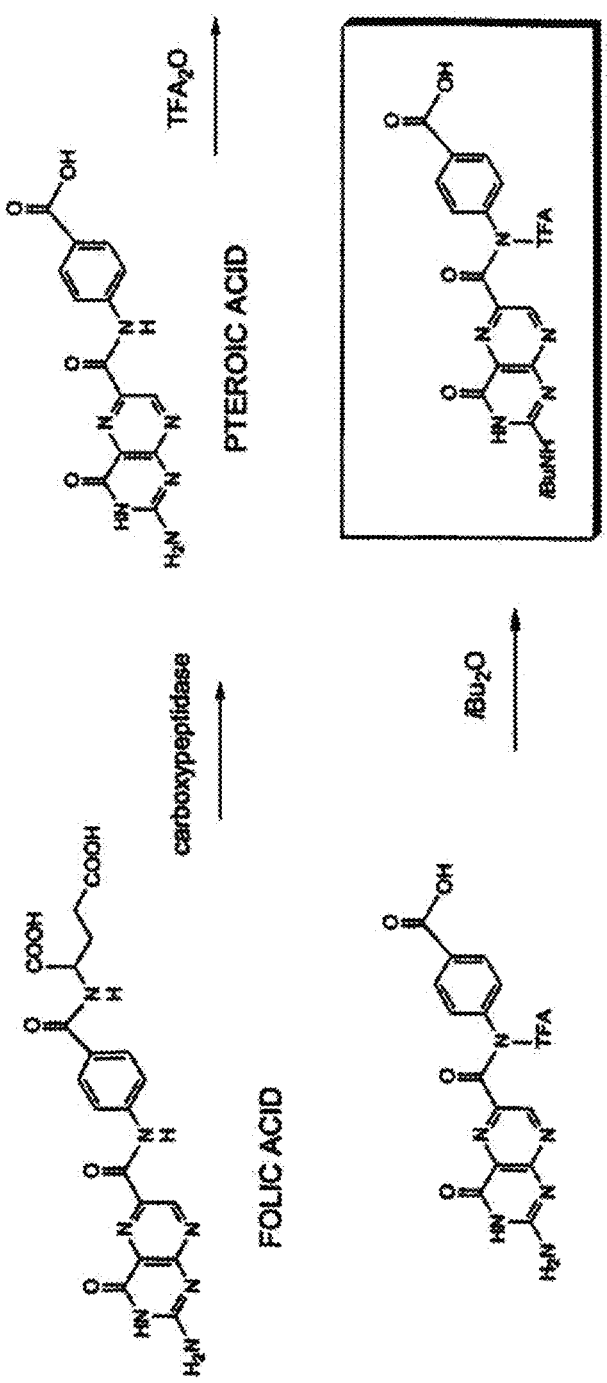
FIG. 8 shows a synthetic scheme for generating a protected pteroic acid synthon of the invention.

Synthesis of $O^1$-(4-monomethoxytrityl)-N-(6-(N-($\alpha$-OFm-L-glutamyl)aminocaproyl))-D-threoninol-$N^2$-iBu-$N^{10}$-TFA-pteroic acid conjugate 3'-O-2-cyanoethyl-N,N-diisopropylphosphor-amidite) (20) (FIG. 5)

General. All reactions were carried out under a positive pressure of argon in anhydrous solvents. Commercially available reagents and anhydrous solvents were used without further purification. $^1$H (400.035 MHz) and $^{31}$P (161.947 MHz) NMR spectra were recorded in $CDCl_3$, unless stated otherwise, and chemical shifts in ppm refer to TMS and $H_3PO_4$, respectively. Analytical thin-layer chromatography (TLC) was performed with Merck Art.5554 Kieselgel 60 F254 plates and flash column chromatography using Merck 0.040-0.063 mm silica gel 60.

N-(N-Fmoc-6-aminocaproyl)-D-threoninol (13). N-Fmoc-6-aminocaproic acid (10 g, 28.30 mmol) was dissolved in DMF (50 ml) and N-hydroxysuccinimide (3.26 g, 28.30 mmol) and 1,3-dicyclohexylcarbodiimide (5.84 g, 28.3 mmol) were added to the solution. The reaction mixture was stirred at RT (about 23° C.) overnight and the precipitated 1,3-dicyclohexylurea filtered off. To the filtrate D-threoninol (2.98 g, 28.30 mmol) was added and the reaction mixture stirred at RT overnight. The solution was reduced to ca half the volume in vacuo, the residue diluted with about m ml of ethyl acetate and extracted with about x ml of 5% NaHCO$_3$, followed by washing with brine. The organic layer was dried (Na$_2$SO$_4$), evaporated to a syrup and chromatographed by silica gel column chromatography using 1-10% gradient of methanol in ethyl acetate. Fractions containing the product were pooled and evaporated to a white solid (9.94 g, 80%). $^1$H-NMR (DMSO-d$_6$-D$_2$O) δ7.97-7.30 (m, 8H, aromatic), 4.34 (d, J=6.80, 2H, Fm), 4.26 (t, J=6.80, 1H, Fm), 3.9 (m, 1H, H3 Thr), 3.69 (m, 1H, H2 Thr), 3.49 (dd, J=10.6, J=7.0, 1H, H1 Thr), 3.35 (dd, J=10.6, J=6.2, 1H, H1' Thr), 3.01 (m, 2H, CH$_2$CO Acp), 2.17 (m, 2H, CH$_2$NH Acp), 1.54 (m, 2H, CH$_2$ Acp), 1.45 (m, 2H, CH$_2$ Acp), 1.27 (m, 2H, CH$_2$ Acp), 1.04 (d, J=6.4, 3H, CH$_3$). MS/ESI$^+$ m/z 441.0 (M+H)$^+$.

O$^1$-(4-Monomethoxytrityl)-N-(N-Fmoc-6-aminocaproyl)-D-threoninol (14). To the solution of 13 (6 g, 13.62 mmol) in dry pyridine (80 ml) p-anisylchlorodiphenyl-methane (6 g, 19.43 mmol) was added and the reaction mixture stirred at RT overnight. Methanol was added (20 ml) and the solution concentrated in vacuo. The residual syrup was partitioned between about x ml of dichloromethane and about x ml of 5% NaHCO$_3$, the organic layer was washed with brine, dried (Na$_2$SO$_4$) and evaporated to dryness. Flash column chromatography using 1-3% gradient of methanol in dichloromethane afforded 14 as a white foam (6 g, 62%). $^1$H-NMR (DMSO) δ7.97-6.94 (m, 22H, aromatic), 4.58 (d, 1H, J=5.2, OH), 4.35 (d, J=6.8, 2H, Fm), 4.27 (t, J=6.8, 1H, Fm), 3.97 (m, 2H, H2, H3 Thr), 3.80 (s, 3H, OCH$_3$), 3.13 (dd, J=8.4, J=5.6, 1H, H1 Thr), 3.01 (m, 2H, CH$_2$CO Acp), 2.92 (m, dd, J=8.4, J=6.4, 1H, H1' Thr), 2.21 (m, 2H, CH$_2$NH Acp), 1.57 (m, 2H, CH$_2$ Acp), 1.46 (m, 2H, CH$_2$ Acp), 1.30 (m, 2H, CH$_2$ Acp), 1.02 (d, J=5.6, 3H, CH$_3$). MS/ESI$^+$ m/z 735.5 (M+Na)$^+$.

O'-(4-Monomethoxytrityl)-N-(6-aminocaproyl)-D-threoninol (15). 14 (9.1 g, 12.77 mmol) was dissolved in DMF (100 ml) containing piperidine (10 ml) and the reaction mixture was kept at RT for about 1 hour. The solvents were removed in vacuo and the residue purified by silica gel column chromatography using 1-10% gradient of methanol in dichloromethane to afford 15 as a syrup (4.46 g, 71%). $^1$H-NMR δ7.48-6.92 (m, 14H, aromatic), 6.16 (d, J=8.8, 1H, NH), 4.17 (m, 1H, H3 Thr), 4.02 (m, 1H, H2 Thr), 3.86 (s, 3H, OCH$_3$), 3.50 (dd, J=9.7, J=4.4, 1H, H1 Thr), 3.37 (dd, J=9.7, J=3.4, 1H, H1' Thr), 2.78 (t, J=6.8, 2H, CH$_2$CO Acp), 2.33 (t, J=7.6, 2H, CH$_2$NH Acp), 1.76 (m, 2H, CH$_2$ Acp), 1.56 (m, 2H, CH$_2$ Acp), 1.50 (m, 2H, CH$_2$ Acp), 1.21 (d, J=6.4, 3H, CH$_3$). MS/EST$^+$ m/z 491.5 (M+H)$^+$.

O$^1$-(4-Monomethoxytrityl)-N-(6-(N-(N-Boc-α-OFm-L-glutamyl)aminocaproyl))-D-threoninol (16). To the solution of N-Boc-α-OFm-glutamic acid (Bachem) (1.91 g, 4.48 mmol) in DMF (10 ml) N-hydroxysuccinimide (518 mg, 4.50 mmol) and 1,3-dicyclohexylcarbodiimide (928 mg, 4.50 mmol) was added and the reaction mixture was stirred at RT overnight. 1,3-Dicyclohexylurea was filtered off and to the filtrate 15 (2 g, 4.08 mmol) and pyridine (2 ml) were added. The reaction mixture was stirred at RT for 3 hours and than concentrated in vacuo. The residue was partitioned between ethyl acetate and 5% Na$_2$HCO$_3$, the organic layer extracted with brine as previously described, dried (Na$_2$SO$_4$) and evaporated to a syrup. Column chromatography using 2-10% gradient of methanol in dichlotomethane afforded 16 as a white foam (3.4 g, 93%). $^1$H-NMR δ7.86-6.91 (m, 22H, aromatic), 6.13 (d, J=8.8, 1H, NH), 5.93 (br s, 1H, NH), 5.43 (d, J=8.4, 1H, NH), 4.63 (dd, J=10.6, J=6.4, 1H, Fm), 4.54 (dd, J=10.6, J=6.4, 1H, Fm), 4.38 (m, 1H, Glu), 4.3 (t, J=6.4, 1H, Fm), 4.18 (m, 1H, H3 Thr), 4.01 (m, 1H, H2 Thr), 3.88 (s, 3H, OCH$_3$), 3.49 (dd, J=9.5, J=4.4, 1H, H1 Thr), 3.37 (dd, J=9.5, J=3.8, 1H, H1' Thr), 3.32 (m, 2H, CH$_2$CO Acp), 3.09 (br s, 1H, OH), 2.32 (m, 2H, CH$_2$NH Acp), 2.17 (m, 3H, Glu), 1.97 (m, 1H, Glu), 1.77 (m, 2H, CH$_2$ Acp), 1.61 (m, 2H, CH$_2$ Acp), 1.52 (s, 9H, t-Bu), 1.21 (d, J=6.4, 3H, CH$_3$). MS/ESI$^+$ m/z 920.5 (M+Na)$^+$.

N-(6-(N-α-OFm-L-glutamyl)aminocaproyl))-D-threoninol hydrochloride (17). 16 (2 g, 2.23 mmol) was dissolved in methanol (30 ml) containing anisole (10 ml) and to this solution x ml of 4M HCl in dioxane was added. The reaction mixture was stirred for 3 hours at RT and then concentrated in vacuo. The residue was dissolved in ethanol and the product precipitated by addition of x ml of ether. The precipitate was washed with ether and dried to give 17 as a colorless foam (1 g, 80%). $^1$H-NMR (DMSO-d$_6$-D$_2$O) δ7.97-7.40 (m, 8H, aromatic), 4.70 (m, 1H, Fm), 4.55 (m, 1H, Fm), 4.40 (t, J=6.4, 1H, Fm), 4.14 (t, J=6.6, 1H, Glu), 3.90 (dd, J=2.8, J=6.4, 1H, H3 Thr), 3.68 (m, 1H, H2 Thr), 3.49 (dd, J=10.6, J=7.0, 1H, H1 Thr), 3.36 (dd, J=10.6, J=6.2, 1H, H1' Thr), 3.07 (m, 2H, CH$_2$CO Acp), 2.17 m, 3H), 1.93 (m, 2H), 1.45 (m, 2H), 1.27 (m, 2H), 1.04 (d, J=6.4, 3H Thr). MS/EST$^+$ m/z 526.5 (M+H)$^+$.

N-(6-(N-α-OFm-L-glutamyl)aminocaproyl))-D-threoninol-N$^2$-iBu-N$^{10}$-TFA-pteroic acid conjugate (18). To the solution of N$^2$-iBu-N$^{10}$-TFA-pteroic acid' (480 mg, 1 mmol) in DMF (5 ml) 1-hydroxybenzotriazole (203 mg, 1.50 mmol), EDCI (288 mg, 1.50 mmol) and 17 (free base, 631 mg, 1.2 mmol) are added. The reaction mixture is stirred at RT for 2 hours, then concentrated to ca 3 ml and loaded on the column of silica gel. Elution with dichloromethane, followed by 1-20% gradient of methanol in dichloromethane afforded 18 (0.5 g, 51%). $^1$H-NMR (DMSO-d$_6$-D$_2$O) δ 9.09 (d, J=6.8, 1H, NH) 8.96 (s, 1H, H7 pteroic acid), 8.02-7.19 (m, 13H, aromatic, NH), 5.30 (s, 2H, pteroic acid), 4.50 (m, 1H, Glu), 4.41 (d, J=6.8, 2H, Fm), 4.29 (t, J=6.8, 1H, Fm), 3.89 (dd, J=6.2, J=2.8, 1H, H3 Thr), 3.68 (m, 1H, H2 Thr), 3.48 (dd, J=10.4, J=7.0, 1H, H1 Thr), 3.36 (dd, J=10.4, J=6.2, 1H H1' Thr), 3.06 (m, 2H, CH$_2$CO Acp), 2.84 (m, 1H, iBu), 2.25 (m, 2H, CH$_2$NH Acp), 2.16 (m, 3H, Glu), 1.99 (m, 1H, Glu), 1.52 (m, 2H Acp), 1.42 (m, 2H Acp), 1.27 (m, 2H Acp), 1.20 (s, 3H iBu), 1.19 (s, 3H, iBu), 1.03 (d, J=6.2, 3H Thr). MS/ESI$^-$ m/z 984.5 (M–H)$^-$.

O$^1$-(4-monomethoxytrityl)-N-(6-(N-α-OFm-L-glutamyl)aminocaproyl))-D-threoninol-N$^2$-iBu-N$^{10}$-TFA-pteroic acid conjugate (19). To the solution of conjugate 18 (1 g, 1.01 mmol) in dry pyridine (15 ml) p-anisylchlorodiphenylmethane (405 mg) was added and the reaction mixture was stirred, protected from moisture, at RT overnight. Methanol (3 ml) was added and the reaction mixture concentrated to a syrup in vacuo. The residue was partitioned between dichloromethane and 5% NaHCO$_3$, the organic layer washed with brine, dried (Na$_2$SO$_4$) and evaporated to dryness. Column chromatography using 0.5-10% gradient of methanol in dichloromethane afforded 19 as a colorless foam (0.5 g, 39%). $^1$H-NMR (DMSO-d$_6$-D$_2$O δ9.09 (d, J=6.8, 1H, NH) 8.94 (s, 1H, H7 pteroic acid), 8.00-6.93 (m, 27H, aromatic, NH), 5.30 (s, 2H, pteroic acid), 4.50 (m, 1H, Glu), 4.40 (d, J=6.8, 2H, Fm), 4.29 (t, J=6.8, 1H, Fm), 3.94 (m, 2H, H3, H2 Thr), 179 (s, 3H, OCH$_3$) 3.11 (dd, J=8.6, J=5.8, 1H, H1 Thr), 3.04 (m, 2H, CH$_2$CO Acp), 2.91 (m, J=8.6, J=6.4, 1H, H1' Thr), 2.85 (m, 1H, iBu), 2.25 (m, 2H, CH$_2$NH Acp), 2.19 (m, 2H, Glu), 2.13 (m, 1H, Glu), 1.98 (m, 1H, Glu), 1.55 (m, 2H Acp), 1.42 (m, 211 Acp), 1.29 (m, 2H Acp), 1.20 (s, 3H iBu), 1.18 (s, 3H, iBu), 1.00 (d, J=6.4, 3H Thr). MS/ESI⁻ m/z 1257.0 (M−H)⁻.

$O^1$-(4-monomethoxytrityl)-N-(6-(N-α-OFm-L-glutamyl) aminocaproyl))-D-threoninol-$N^2$-iBu-$N^{10}$-TFA-pteroic acid conjugate 3'-O-(2-cyanoethyl-N,N-diisopropylphosphoramidite) (20). To the solution of 19 (500 mg, 0.40 mmol) in dichloromethane (2 ml) 2-cyanoethyl tetraisopropylphosphordiamidite (152 μL, 0.48 mmol) was added followed by pyridinium trifluoroacetate (93 mg, 0.48 mmol). The reaction mixture was stirred at RT for 1 hour and than loaded on the column of silica gel in hexanes. Elution using ethyl acetate-hexanes 1:1, followed by ethyl acetate and ethyl acetate-acetone 1:1 in the presence of 1% pyridine afforded 20 as a colorless foam (480 mg, 83%). $^{31}$P NMR δ 149.4 (s), 149.0 (s).

Example 2

Figure 9:
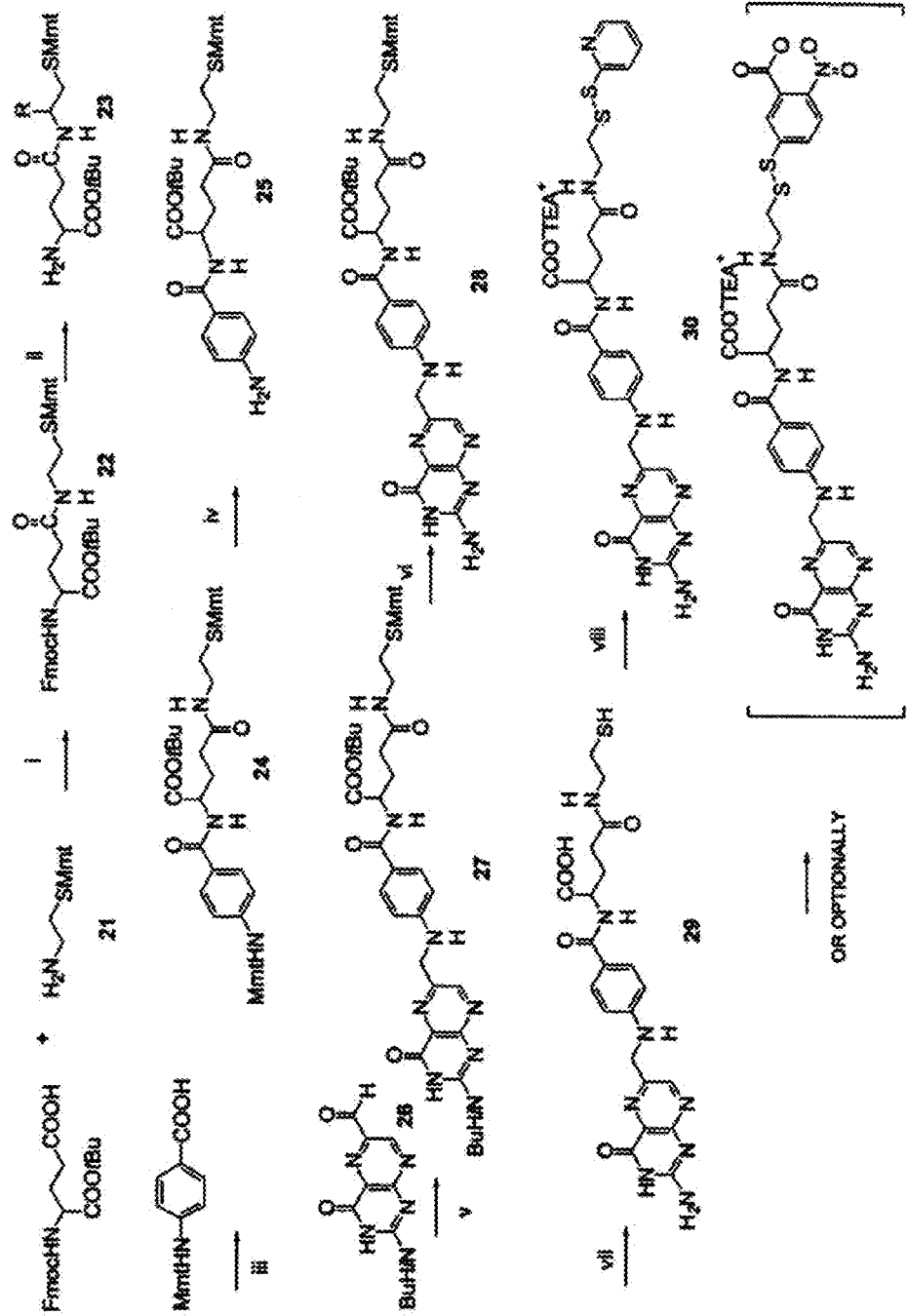
FIG. 9 shows a synthetic scheme for generating a 2-dithiopyridyl activated folic acid synthon of the invention.

Synthesis of 2-dithiopyridyl activated folic acid (30) (FIG. 9)

Synthesis of the cysteamine modified folate 30 is presented in FIG. 9. Monomethoxytrityl cysteamine 21 was prepared by selective tritylation of the thiol group of cysteamine with 4-methoxytrityl alcohol in trifluoroacetic acid. Peptide coupling of 21 with Fmoc-Glu-OtBu (Bachem Bioscience Inc., King of Prussia, Pa.) in the presence of PyBOP yielded 22 in a high yield. N-Fmoc group was removed smoothly with piperidine to give 23. Condensation of 23 with p-(4-methoxytrityl)aminobenzoic acid, prepared by reaction of p-aminobenzoic acid with 4-methoxytrityl chloride in pyridine, afforded the fully protected conjugate 24. Selective cleavage of N-MMTr group with acetic acid afforded 25 in quantitative yield. Shiff base formation between 25 and $N^2$-iBu-6-formylpterin 26,[9] followed by reduction with borane-pyridine complex proceeded with a good yield to give fully protected cysteamine-folate adduct 27.[12] The consecutive cleavage of protecting groups of 27 with base and acid yielded thiol derivative 29. The thiol exchange reaction of 29 with 2,2-dipyridyl disulfide afforded the desired S-pyridyl activated synthon 30 as a yellow powder; Isolated as a TEA⁺ salt: $^1$H NMR spectrum for 10 in $D_2O$: δ 8.68 (s, 1 H, H-7), 8.10 (d, J=3.6, 1 H, pyr), 7.61 (d, J=8.8, 2 H, PABA), 7.43 (m, 1 H, pyr), 7.04 (d, J=7.6, 1 H, pyr), 6.93 (m, 1 H, pyr), 6.82 (d, J=8.8, 1 H, PABA), 4.60 (s, 2 H, 6-$CH_2$), 4.28 (m, 1 H, Glu), 3.30-3.08 (m, 2H, cysteamine), 3.05 (m, 6 H, TEA), 2.37 (m, 2 H, cysteamine), 2.10 (m, 4 H, Glu), 1.20 (m, 9 H, TEA). MS/ESC m/z 608.02 [M−H]⁻. It is worth noting that the isolation of 30 as its TEA⁺ or Na⁺ salt made it soluble in DMSO and/or water, which is an important requirement for its use in conjugation reactions.

Example 3

Figure 10:
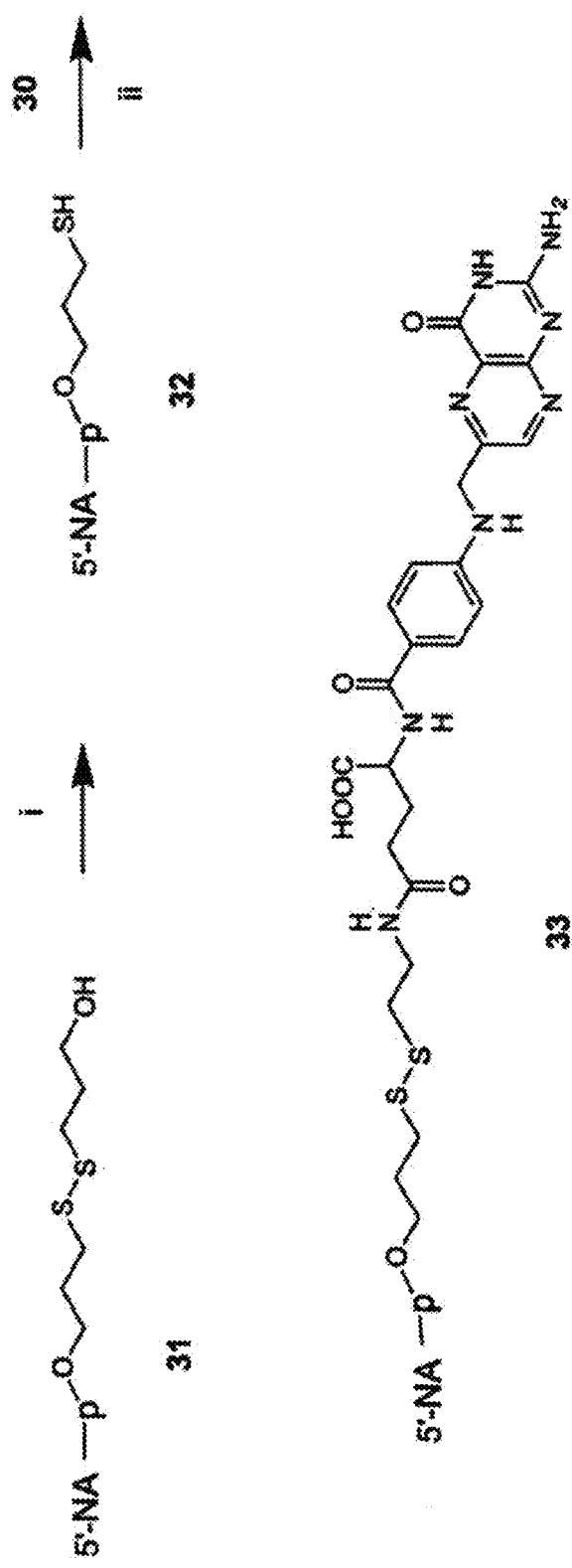
FIG. 10 shows a synthetic scheme for generating an oligonucleotide or nucleic acid-folate conjugate.

Post Synthetic Conjugation of Enzymatic Nucleic Acid to Form Nucleic Acid-Folate Conjugate (33) (FIG. 10)

Figure 11:
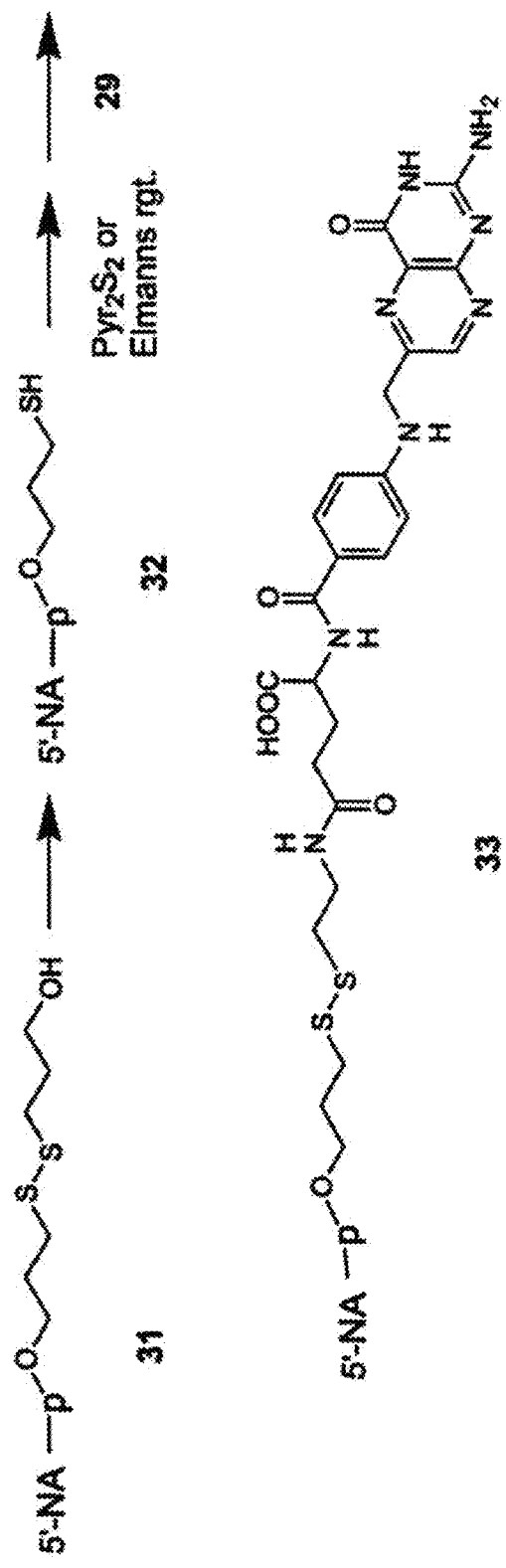
FIG. 11 shows a an alternative synthetic scheme for generating an oligonucleotide or nucleic acid-folate conjugate.

Oligonucleotide synthesis, deprotection and purification was performed as described herein. 5'-Thiol-Modifier C6 (Glen Research, Sterling, Va.) was coupled as the last phosphoramidite to the 5'-end of a growing oligonucleotide chain. After cleavage from the solid support and base deprotection, the disulfide modified enzymatic nucleic acid molecule 31 (FIG. 10) was purified using ion exchange chromatography. The thiol group was unmasked by reduction with dithiothreitol (DTT) to afford 32 which was purified by gel filtration and immediately conjugated with 30. The resulting conjugate 33 was separated from the excess folate by gel filtration and then purified by RP HPLC using gradient of acetonitrile in 50 mM triethylammonium acetate (TEAA). Desalting was performed by RP HPLC. Reactions were conducted on 400 mg of disulfide modified enzymatic nucleic acid molecule 31 to afford 200-250 mg (50-60% yield) of conjugate 33. MALDI TOF MS confirmed the structure: 13 [M−H]⁻ 12084.74 (calc. 12083.82). An alternative approach to this synthesis is shown in FIG. 11.

As shown in Examples 2 and 3, a folate-cysteamine adduct can be prepared by a scaleable solution phase synthesis in a good overall yield. Disulfide conjugation of this novel targeting ligand to the thiol-modified oligonucleotide is suitable for the multi-gram scale synthesis. The 9-atom spacer provides a useful spatial separation between folate and attached oligonucleotide cargo. Importantly, conjugation of folate to the oligonucleotide through a disulfide bond should permit intermolecular separation which was suggested to be required for the functional cytosolic entry of a protein drug.

One skilled in the art would readily appreciate that the present invention is well adapted to carry out the objects and obtain the ends and advantages mentioned, as well as those inherent therein. The methods and compositions described herein are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Other embodiments are within the following claims.

TABLE I

Characteristics of naturally occurring ribozymes

Group I Introns

Size: ~150 to >1000 nucleotides.
Requires a U in the target sequence immediately 5' of the cleavage site.
Binds 4-6 nucleotides at the 5'-side of the cleavage site.
Reaction mechanism: attack by the 3'-OH of guanosine to generate cleavage products with 3'-OH and 5'-guanosine.
Additional protein cofactors required in some cases to help folding and maintenance of the active structure.
Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [i, ii].
Complete kinetic framework established for one ribozyme [iii, iv, v, vi].
Studies of ribozyme folding and substrate docking underway [vii, viii, ix].
Chemical modification investigation of important residues well established [x, xi].
The small (4-6 nt) binding site may make this ribozyme too non-specific for targeted RNA cleavage, however, the *Tetrahymena* group I intron has been used to repair a "defective" β-galactosidase message by the ligation of new β-galactosidase sequences onto the defective message [xii].

RNAse P RNA (M1 RNA)

Size: ~290 to 400 nucleotides.
RNA portion of a ubiquitous ribonucleoprotein enzyme.
Cleaves tRNA precursors to form mature tRNA [xiii].
Reaction mechanism: possible attack by $M^{2+}$-OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P for therapeutic applications is possible through hybridization of an External Guide Sequence (EGS) to the target RNA [xiv, xv]
Important phosphate and 2' OH contacts recently identified [xvi, xvii]

Group II Introns

Size: >1000 nucleotides.
Trans cleavage of target RNAs recently demonstrated [xviii, xix].
Sequence requirements not fully determined.
Reaction mechanism: 2'-OH of an internal adenosine generates cleavage products with 3'-OH and a "lariat" RNA containing a 3'-5' and a 2'-5' branch point.
Only natural ribozyme with demonstrated participation in DNA cleavage [xx, xxi] in addition to RNA cleavage and ligation.
Major structural features largely established through phylogenetic comparisons [xxii].
Important 2' OH contacts beginning to be identified [xxiii]
Kinetic framework under development [xxiv]

Neurospora VS RNA

Size: ~144 nucleotides.
Trans cleavage of hairpin target RNAs recently demonstrated [xxv].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.

Hammerhead Ribozyme
(see text for references)

Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissile bond to generate cleavage products with 2',3'-cyclic phosphate and 5'-OH ends.
14 known members of this class. Found in a number of plant pathogens (virusoids) that use RNA as the infectious agent.
Essential structural features largely defined, including 2 crystal structures [xxvi, xxvii]
Minimal ligation activity demonstrated (for engineering through in vitro selection) [xxviii]
Complete kinetic framework established for two or more ribozymes [xxix].
Chemical modification investigation of important residues well established [xxx].

Hairpin Ribozyme

Size: ~50 nucleotides.
Requires the target sequence GUC immediately 3' of the cleavage site.
Binds 4-6 nucleotides at the 5'-side of the cleavage site and a variable number to the 3'-side of the cleavage site.

TABLE I-continued

Characteristics of naturally occurring ribozymes

Reaction mechanism: attack by 2'-OH 5' to the scissile bond to generate cleavage products with 2',3'-cyclic phosphate and 5'-OH ends.
3 known members of this class. Found in three plant pathogen (satellite RNAs of the tobacco ringspot virus, arabis mosaic virus and chicory yellow mottle virus) which uses RNA as the infectious agent.
Essential structural features largely defined [xxxi, xxxii, xxxiii, xxxiv]
Ligation activity (in addition to cleavage activity) makes ribozyme amenable to engineering through in vitro selection [xxxv]
Complete kinetic framework established for one ribozyme [xxxvi].
Chemical modification investigation of important residues begun [xxxvii, xxxviii].

Hepatitis Delta Virus (HDV) Ribozyme

Size: ~60 nucleotides.
Trans cleavage of target RNAs demonstrated [xxxix].
Binding sites and structural requirements not fully determined, although no sequences 5' of cleavage site are required. Folded ribozyme contains a pseudoknot structure [xl].
Reaction mechanism: attack by 2'-OH 5' to the scissile bond to generate cleavage products with 2',3'-cyclic phosphate and 5'-OH ends.
Only 2 known members of this class. Found in human HDV.
Circular form of HDV is active and shows increased nuclease stability [xli]

---

[i] Michel, Francois; Westhof, Eric. Slippery substrates. Nat. Struct. Biol. (1994), 1(1), 5-7.
[ii] Lisacek, Frederique; Diaz, Yolande; Michel, Francois. Automatic identification of group I intron cores in genomic DNA sequences. J. Mol. Biol. (1994), 235(4), 1206-17.
[iii] Herschlag, Daniel; Cech, Thomas R.. Catalysis of RNA cleavage by the *Tetrahymena thermophila* ribozyme. 1. Kinetic description of the reaction of an RNA substrate complementary to the active site. Biochemistry (1990), 29(44), 10159-71.
[iv] Herschlag, Daniel; Cech, Thomas R.. Catalysis of RNA cleavage by the *Tetrahymena thermophila* ribozyme. 2. Kinetic description of the reaction of an RNA substrate that forms a mismatch at the active site. Biochemistry (1990), 29(44), 10172-80.
[v] Knitt, Deborah S.; Herschlag, Daniel. pH Dependencies of the *Tetrahymena* Ribozyme Reveal an Unconventional Origin of an Apparent pKa. Biochemistry (1996), 35(5), 1560-70.
[vi] Bevilacqua, Philip C.; Sugimoto, Naoki; Turner, Douglas H.. A mechanistic framework for the second step of splicing catalyzed by the *Tetrahymena* ribozyme. Biochemistry (1996), 35(2), 648-58.
[vii] Li, Yi; Bevilacqua, Philip C.; Mathews, David; Turner, Douglas H.. Thermodynamic and activation parameters for binding of a pyrene-labeled substrate by the *Tetrahymena* ribozyme: docking is not diffusion-controlled and is driven by a favorable entropy change. Biochemistry (1995), 34(44), 14394-9.
[viii] Banerjee, Aloke Raj; Turner, Douglas H.. The time dependence of chemical modification reveals slow steps in the folding of a group I ribozyme. Biochemistry (1995), 34(19), 6504-12.
[ix] Zarrinkar, Patrick P.; Williamson, James R.. The P9.1-P9.2 peripheral extension helps guide folding of the *Tetrahymena* ribozyme. Nucleic Acids Res. (1996), 24(5), 854-8.
[x] Strobel, Scott A.; Cech, Thomas R.. Minor groove recognition of the conserved G.cntdot.U pair at the *Tetrahymena* ribozyme reaction site. Science (Washington, D.C.) (1995), 267(5198), 675-9.
[xi] Strobel, Scott A.; Cech, Thomas R.. Exocyclic Amine of the Conserved G.cntdot.U Pair at the Cleavage Site of the *Tetrahymena* Ribozyme Contributes to 5'-Splice Site Selection and Transition State Stabilization. Biochemistry (1996), 35(4), 1201-11.
[xii] Sullenger, Bruce A.; Cech, Thomas R.. Ribozyme-mediated repair of defective mRNA by targeted trans-splicing. Nature (London) (1994), 371(6498), 619-22.
[xiii] Robertson, H. D.; Altman, S.; Smith, J. D. J. Biol. Chem., 247, 5243-5251 (1972).
[xiv] Forster, Anthony C.; Altman, Sidney. External guide sequences for an RNA enzyme. Science (Washington, D.C., 1883-) (1990), 249(4970), 783-6.
[xv] Yuan, Y.; Hwang, E. S.; Altman, S. Targeted cleavage of mRNA by human RNase P. Proc. Natl. Acad. Sci. USA (1992) 89, 8006-10.
[xvi] Harris, Michael E.; Pace, Norman R.. Identification of phosphates involved in catalysis by the ribozyme RNase P RNA. RNA (1995), 1(2), 210-18.
[xvii] Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510-14.
[xviii] Pyle, Anna Marie; Green, Justin B.. Building a Kinetic Framework for Group II Intron Ribozyme Activity: Quantitation of Interdomain Binding and Reaction Rate. Biochemistry (1994), 33(9), 2716-25.
[xix] Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965-77.
[xx] Zimmerly, Steven; Guo, Huatao; Eskes, Robert; Yang, Jian; Perlman, Philip S.; Lambowitz, Alan M.. A group II intron RNA is a catalytic component of a DNA endonuclease involved in intron mobility. Cell (Cambridge, Mass.) (1995), 83(4), 529-38.
[xxi] Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761-70.
[xxii] Michel, Francois; Ferat, Jean Luc. Structure and activities of group II introns. Annu. Rev. Biochem. (1995), 64, 435-61.
[xxiii] Abramovitz, Dana L.; Friedman, Richard A.; Pyle, Anna Marie. Catalytic role of 2'-hydroxyl groups within a group II intron active site. Science (Washington, D.C.) (1996), 271(5254), 1410-13.
[xxiv] Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256(1), 31-49.
[xxv] Guo, Hans C. T.; Collins, Richard A.. Efficient trans-cleavage of a stem-loop RNA substrate by a ribozyme derived from Neurospora VS RNA. EMBO J. (1995), 14(2), 368-76.
[xxvi] Scott, W. G., Finch, J. T., Aaron, K. The crystal structure of an all RNA hammerhead ribozyme: A proposed mechanism for RNA catalytic cleavage. Cell, (1995), 81, 991-1002.
[xxvii] McKay, Structure and function of the hammerhead ribozyme: an unfinished story. RNA, (1996), 2, 395-403.
[xxviii] Long, D., Uhlenbeck, O., Hertel, K. Ligation with hammerhead ribozymes. U.S. Pat. No. 5,633,133.
[xxix] Hertel, K. J., Herschlag, D., Uhlenbeck, O. A kinetic and thermodynamic framework for the hammerhead ribozyme reaction. Biochemistry, (1994) 33, 3374-3385. Beigelman, L., et al., Chemical modifications of hammerhead ribozymes. J. Biol. Chem., (1995) 270, 25702-25708.
[xxx] Beigelman, L., et al., Chemical modifications of hammerhead ribozymes. J. Biol. Chem., (1995) 270, 25702-25708.
[xxxi] Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299-304.
[xxxii] Chowrira, Bharat M.; Berzal-Herranz, Alfredo; Burke, John M.. Novel guanosine requirement for catalysis by the hairpin ribozyme. Nature (London) (1991), 354(6351), 320-2.
[xxxiii] Berzal-Herranz, Alfredo; Joseph, Simpson; Chowrira, Bharat M.; Butcher, Samuel E.; Burke, John M.. Essential nucleotide sequences and secondary structure elements of the hairpin ribozyme. EMBO J. (1993), 12(6), 2567-73.

TABLE I-continued

Characteristics of naturally occurring ribozymes

[xxxiv] Joseph, Simpson; Berzal-Herranz, Alfredo; Chowrira, Bharat M.; Butcher, Samuel E.. Substrate selection rules for the hairpin ribozyme determined by in vitro selection, mutation, and analysis of mismatched substrates. Genes Dev. (1993), 7(1), 130-8.

[xxxv] Berzal-Herranz, Alfredo; Joseph, Simpson; Burke, John M.. In vitro selection of active hairpin ribozymes by sequential RNA-catalyzed cleavage and ligation reactions. Genes Dev. (1992), 6(1), 129-34.

[xxxvi] Hegg, Lisa A.; Fedor, Martha J.. Kinetics and Thermodynamics of Intermolecular Catalysis by Hairpin Ribozymes. Biochemistry (1995), 34(48), 15813-28.

[xxxvii] Grasby, Jane A.; Mersmann, Karin; Singh, Mohinder; Gait, Michael J.. Purine Functional Groups in Essential Residues of the Hairpin Ribozyme Required for Catalytic Cleavage of RNA. Biochemistry (1995), 34(12), 4068-76.

[xxxviii] Schmidt, Sabine; Beigelman, Leonid; Karpeisky, Alexander; Usman, Nassim; Sorensen, Ulrik S.; Gait, Michael J.. Base and sugar requirements for RNA cleavage of essential nucleoside residues in internal loop B of the hairpin ribozyme: implications for secondary structure. Nucleic Acids Res. (1996), 24(4), 573-81.

[xxxix] Perrotta, Anne T.; Been, Michael D.. Cleavage of oligoribonucleotides by a ribozyme derived from the hepatitis .delta. virus RNA sequence. Biochemistry (1992), 31(1), 16-21.

[xl] Perrotta, Anne T.; Been, Michael D.. A pseudoknot-like structure required for efficient self-cleavage of hepatitis delta virus RNA. Nature (London) (1991), 350(6317), 434-6.

[xli] Puttaraju, M.; Perrotta, Anne T.; Been, Michael D.. A circular trans-acting hepatitis delta virus ribozyme. Nucleic Acids Res. (1993), 21(18), 4253-8.

TABLE II

A. 2.5 μmol Synthesis Cycle ABI 394 Instrument

| Reagent | Equivalents | Amount | Wait Time* DNA | Wait Time* 2'-O-methyl | Wait Time* RNA |
|---|---|---|---|---|---|
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |

B. 0.2 μmol Synthesis Cycle ABI 394 Instrument

| Reagent | Equivalents | Amount | Wait Time* DNA | Wait Time* 2'-O-methyl | Wait Time* RNA |
|---|---|---|---|---|---|
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

C. 0.2 μmol Synthesis Cycle 96 well Instrument

| Reagent | Equivalents: DNA/ 2'-O-methyl/Ribo | Amount: DNA/ 2'-O-methyl/Ribo | Wait Time* DNA | Wait Time* 2'-O-methyl | Wait Time* Ribo |
|---|---|---|---|---|---|
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 | 100 sec | 200 sec | 200 sec |
| Acetonitrile | NA | 1150/1150/1150 μL | NA | NA | NA |

*Wait time does not include contact time during delivery.

The invention claimed is:

1. A compound having formula XXV:

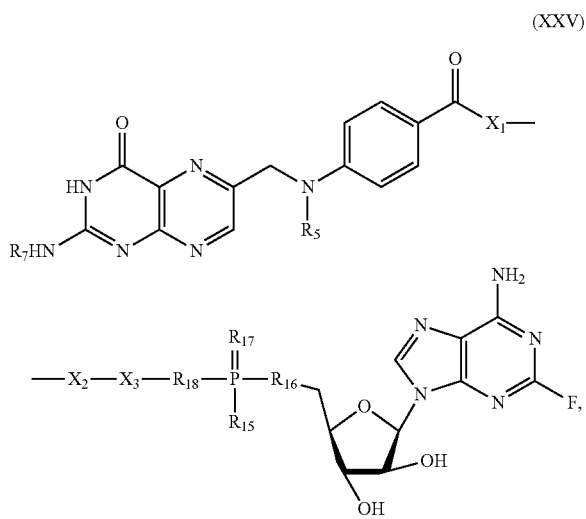

(XXV)

wherein each of $R_5$ and $R_7$ is independently selected from the group consisting of hydrogen, alkyl and a nitrogen protecting group;

each of $R_{15}$, $R_{16}$, $R_{17}$ and $R_{18}$ is independently selected from the group consisting of O, S, alkyl, substituted alkyl, aryl, substituted aryl and halogen;

$X_1$ is —CH($X_{1'}$) or a group of formula XXVI:

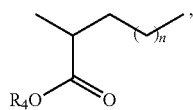

wherein $R_4$ is a protecting group and n is an integer from 0 to 200;

$X_{1'}$ is a protected or unprotected side chain of a naturally occurring or non-naturally occurring amino acid;

$X_2$ is selected from the group consisting of amide, alkyl, or carbonyl containing linker and a bond;

and $X_3$ is a degradable linker which is optionally absent.

2. The compound of claim 1, wherein each of $R_5$ and $R_7$ is independently hydrogen or alkyl.

3. The compound of claim 2, wherein each of $R_5$ and $R_7$ is independently hydrogen or methyl.

4. The compound of claim 1, wherein each of $R_{15}$, $R_{16}$, $R_{17}$ and $R_{18}$ is independently selected from the group consisting of O, S, alkyl and substituted alkyl.

5. The compound of claim 4, wherein each of $R_{15}$, $R_{16}$, $R_{17}$ and $R_{18}$ is independently selected from the group consisting of O, S and alkyl.

6. The compound of claim 4, wherein each of $R_{15}$, $R_{16}$, $R_{17}$ and $R_{18}$ is independently O or S.

7. The compound of claim 1, wherein $X_1$ is a group of formula XXVI:

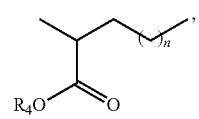

wherein $R_4$ is a protecting group and n is an integer from 0 to about 200.

8. The compound of claim 1, wherein $X_2$ is amide, alkyl, or a bond.

9. The compound of claim 1, wherein $X_3$ is a degradable linker.

10. The compound of claim 1, wherein $X_3$ is a group of formula XXVI:

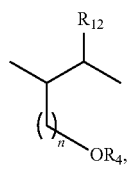

wherein $R_4$ is hydrogen or a protecting group; n is an integer from 0 to about 200; and $R_{12}$ is hydrogen, a straight or branched chain alkyl, aryl, or substituted aryl.

11. The compound of claim 10, wherein $R_4$ is hydrogen and $R_{12}$ is hydrogen or methyl.

* * * * *